United States Patent
Akin et al.

(10) Patent No.: US 10,596,713 B2
(45) Date of Patent: Mar. 24, 2020

(54) ACTUATED SENSOR MODULE AND METHOD FOR IN SITU GAP INSPECTION ROBOTS

(71) Applicant: General Electric Company, Schenectady, NY (US)

(72) Inventors: Selim Akin, Istanbul (TR); Thomas James Batzinger, Burnt Hills, NY (US); Airton Rosa da Silva, Jr., Schenectady, NY (US); Selami Haydar Icli, Zurich (CH); Paulo Cesar Debenest, Tokyo (JP); Michele Guarnieri, Tokyo (JP); Giorgio Valsecchi, Tokyo (JP); Giacomo Cimarelli, Tokyo (JP); Shigeo Hirose, Tokyo (JP)

(73) Assignee: General Electric Company, Schenectady, NY (US)

( * ) Notice: Subject to any disclaimer, the term of this patent is extended or adjusted under 35 U.S.C. 154(b) by 192 days.

(21) Appl. No.: 15/652,805

(22) Filed: Jul. 18, 2017

(65) Prior Publication Data
US 2019/0022877 A1    Jan. 24, 2019

(51) Int. Cl.
*G06F 19/00* (2018.01)
*B25J 19/02* (2006.01)
(Continued)

(52) U.S. Cl.
CPC .......... *B25J 19/023* (2013.01); *B62D 57/02* (2013.01); *G01M 13/00* (2013.01); *G01N 21/00* (2013.01);
(Continued)

(58) Field of Classification Search
CPC ....... B25J 19/023; B62D 55/00; G01M 13/00; G01N 21/00; G01R 31/34; Y10S 901/01; Y10S 901/44; Y10S 901/46
(Continued)

(56) References Cited

U.S. PATENT DOCUMENTS 4,677,865 A    7/1987 Lehmann
4,683,973 A    8/1987 Honjo et al.
(Continued)

FOREIGN PATENT DOCUMENTS

CH      669127 A5    2/1989
EP      0171633 A1   2/1986
(Continued)

OTHER PUBLICATIONS

International Search Report and written opinion for corresponding PCT Application No. PCT/US2018/037900 dated Sep. 13, 2018, 14 pages.
(Continued)

*Primary Examiner* — Ronnie M Mancho
(74) *Attorney, Agent, or Firm* — Theordoros Stamatiadis; Hoffman Warnick LLC

(57) ABSTRACT

This disclosure provides systems and methods for an actuated sensor module for in situ gap inspection robots. A mounting interface attaches to the sensor module to the robot system. A least one arm is operatively connected to the mounting interface and has a joint. A sensor head is operatively connected to the arm at the joint and an actuator operatively connected to the arm moves the sensor head around the second joint.

19 Claims, 11 Drawing Sheets

(51) Int. Cl.
  *G01M 13/00* (2019.01)
  *B62D 57/02* (2006.01)
  *G01N 21/00* (2006.01)
  *B62D 57/024* (2006.01)
(52) U.S. Cl.
  CPC ........... *B62D 57/024* (2013.01); *Y10S 901/01* (2013.01); *Y10S 901/44* (2013.01); *Y10S 901/46* (2013.01)
(58) Field of Classification Search
  USPC ........................................................ 700/259
  See application file for complete search history.

(56) References Cited

U.S. PATENT DOCUMENTS

| | | | |
|---|---|---|---|
| 4,889,000 | A | 12/1989 | Jaafar et al. |
| 4,970,890 | A | 11/1990 | Jaafar et al. |
| 5,172,639 | A | 12/1992 | Wiesman et al. |
| 5,650,579 | A | 7/1997 | Hatley et al. |
| 5,788,002 | A | 8/1998 | Richter |
| 5,947,051 | A * | 9/1999 | Geiger ................... B62D 57/00 114/222 |
| 5,969,531 | A | 10/1999 | Murakami et al. |
| 6,100,711 | A | 8/2000 | Hatley |
| 6,404,189 | B2 | 6/2002 | Kwun et al. |
| 6,814,169 | B2 | 11/2004 | Moore et al. |
| 6,876,222 | B2 | 4/2005 | Fischer et al. |
| 6,889,783 | B1 | 5/2005 | Moore et al. |
| 6,917,176 | B2 | 7/2005 | Schempf et al. |
| 6,959,603 | B2 | 11/2005 | Knight et al. |
| 7,188,568 | B2 | 3/2007 | Stout |
| 7,201,055 | B1 | 4/2007 | Bagley et al. |
| 7,218,993 | B2 | 5/2007 | Yasukawa et al. |
| 7,331,436 | B1 | 2/2008 | Pack et al. |
| 7,520,189 | B2 | 4/2009 | Abbasi et al. |
| 7,600,593 | B2 | 10/2009 | Filippov et al. |
| 7,617,732 | B2 | 11/2009 | Bui et al. |
| 7,624,827 | B2 | 12/2009 | Moser et al. |
| 7,654,348 | B2 | 2/2010 | Ohm et al. |
| 7,681,452 | B2 | 3/2010 | Bagley et al. |
| 7,743,675 | B2 | 6/2010 | Moore |
| 7,866,421 | B2 | 1/2011 | Moore et al. |
| 7,891,445 | B1 | 2/2011 | McKinley et al. |
| 8,028,775 | B2 | 10/2011 | Orenbuch |
| 8,220,345 | B2 | 7/2012 | Moser et al. |
| 8,477,891 | B2 | 7/2013 | Wallace et al. |
| 8,568,299 | B2 * | 10/2013 | Eno ................... A61B 1/00045 600/117 |
| 8,571,711 | B2 | 10/2013 | Jacobsen et al. |
| 8,619,134 | B2 | 12/2013 | Christ |
| 8,839,684 | B2 | 9/2014 | Banowetz et al. |
| 9,031,698 | B2 | 5/2015 | Smith |
| 9,056,746 | B2 | 6/2015 | Mehrandezh et al. |
| 9,217,852 | B2 | 12/2015 | Baleine |
| D748,053 | S | 1/2016 | Herrlich et al. |
| D756,922 | S | 5/2016 | Herrlich et al. |
| 9,398,198 | B2 | 7/2016 | Choi et al. |
| 9,409,292 | B2 | 8/2016 | Smith et al. |
| 9,683,460 | B2 | 6/2017 | Moore et al. |
| 9,708,934 | B2 | 7/2017 | Moore et al. |
| 9,759,667 | B2 | 9/2017 | Miasnikov et al. |
| 9,808,140 | B2 * | 11/2017 | Belson ................. A61B 1/0053 |
| 9,989,970 | B1 | 6/2018 | Morey et al. |
| 2002/0104693 | A1 | 8/2002 | Moore et al. |
| 2002/0190682 | A1 * | 12/2002 | Schempf ............... G01M 3/005 318/568.11 |
| 2004/0020002 | A1 | 2/2004 | Moore et al. |
| 2004/0099175 | A1 | 5/2004 | Perrot et al. |
| 2004/0173116 | A1 | 9/2004 | Ghorbel et al. |
| 2005/0104600 | A1 | 5/2005 | Cotton |
| 2008/0087112 | A1 | 4/2008 | Bagley et al. |
| 2008/0098832 | A1 | 5/2008 | Abbasi et al. |
| 2008/0121041 | A1 | 5/2008 | Smith et al. |
| 2008/0179115 | A1 * | 7/2008 | Ohm ....................... B25J 5/005 180/9.21 |
| 2008/0308324 | A1 | 12/2008 | Moser et al. |
| 2009/0120215 | A1 | 5/2009 | Jacobson et al. |
| 2009/0146680 | A1 | 6/2009 | Moser et al. |
| 2009/0171151 | A1 * | 7/2009 | Choset ............... A61B 1/00006 600/114 |
| 2011/0040427 | A1 | 2/2011 | Ben-Tzvi |
| 2012/0069172 | A1 | 3/2012 | Hudritsch |
| 2012/0205168 | A1 | 8/2012 | Flynn et al. |
| 2013/0231779 | A1 | 9/2013 | Purkayastha et al. |
| 2014/0022374 | A1 | 1/2014 | Brignac et al. |
| 2014/0067185 | A1 | 3/2014 | Tralshawala et al. |
| 2014/0216836 | A1 | 8/2014 | Davies et al. |
| 2014/0345384 | A1 | 11/2014 | Nguyen |
| 2015/0233787 | A1 | 8/2015 | Eakins et al. |
| 2015/0251318 | A1 | 9/2015 | Lv |
| 2015/0323469 | A1 | 11/2015 | Clayton et al. |
| 2016/0075020 | A1 | 3/2016 | Szarski et al. |
| 2016/0239080 | A1 * | 8/2016 | Marcolina ............... G06F 3/011 |
| 2017/0362068 | A1 | 12/2017 | Cheng |
| 2018/0021945 | A1 * | 1/2018 | Pettersen ................. B25J 9/065 700/245 |
| 2018/0313715 | A1 | 11/2018 | Cichosz et al. |

FOREIGN PATENT DOCUMENTS

| | | |
|---|---|---|
| EP | 0390352 A2 | 10/1990 |
| EP | 1863153 A2 | 12/2007 |
| EP | 2345902 A1 | 7/2011 |
| EP | 2743447 A1 | 6/2014 |
| FR | 2355236 A1 | 1/1978 |
| JP | 2007256262 A | 10/2007 |
| WO | 9702452 | 1/1997 |
| WO | 2008076193 A2 | 6/2008 |
| WO | 2015095543 A1 | 6/2015 |
| WO | 2016138529 A1 | 9/2016 |
| WO | 2016141769 A1 | 9/2016 |

OTHER PUBLICATIONS

U.S. Appl. No. 15/652,859, Office Action dated Feb. 19, 2019, (GEEN-0968-US), 17 pages.
International Search Report and written opinion for corresponding PCT Application No. PCT/US2018/041726 dated Oct. 29, 2018, 16 pages.
U.S. Appl. No. 15/652,680, Office Action dated Mar. 18, 2019, (GEEN-0911-US), 22 pages.
International Search Report and written opinion for corresponding PCT Application No. PCT/US2018/035329 dated Sep. 11, 2018, 18 pages.
International Search Report and written opinion for corresponding PCT Application No. PCT/US2018/038453 dated Oct. 25, 2018, 17 pages.
International Search Report and written opinion for corresponding PCT Application No. PCT/US2018/040982 dated Oct. 17, 2018, 15 pages.
U.S. Appl. No. 15/652,730, Notice of Allowance dated May 3, 2019, (GEEN-0912-US), 9 pages.
International Search Report and Written Opinion for PCT Application No. PCT/DK96/00298 dated Oct. 17, 1996, 25 pages.
U.S. Appl. No. 15/652,859, Notice of Allowance dated May 15, 2019, (GEEN-0968-US), 10 pgs.
U.S. Appl. No. 15/652,680, Notice of Allowance dated Jul. 17, 2019, (GEEN-0911-US), 8 pgs.
U.S. Appl. No. 15/652,680, Notice of Allowance dated Jul. 17, 2019, (GEEN-911-US), 8 pgs.
U.S. Appl. No. 15/652,771, Non-Final Office Action dated Sep. 17, 2019, 11 pgs.

* cited by examiner

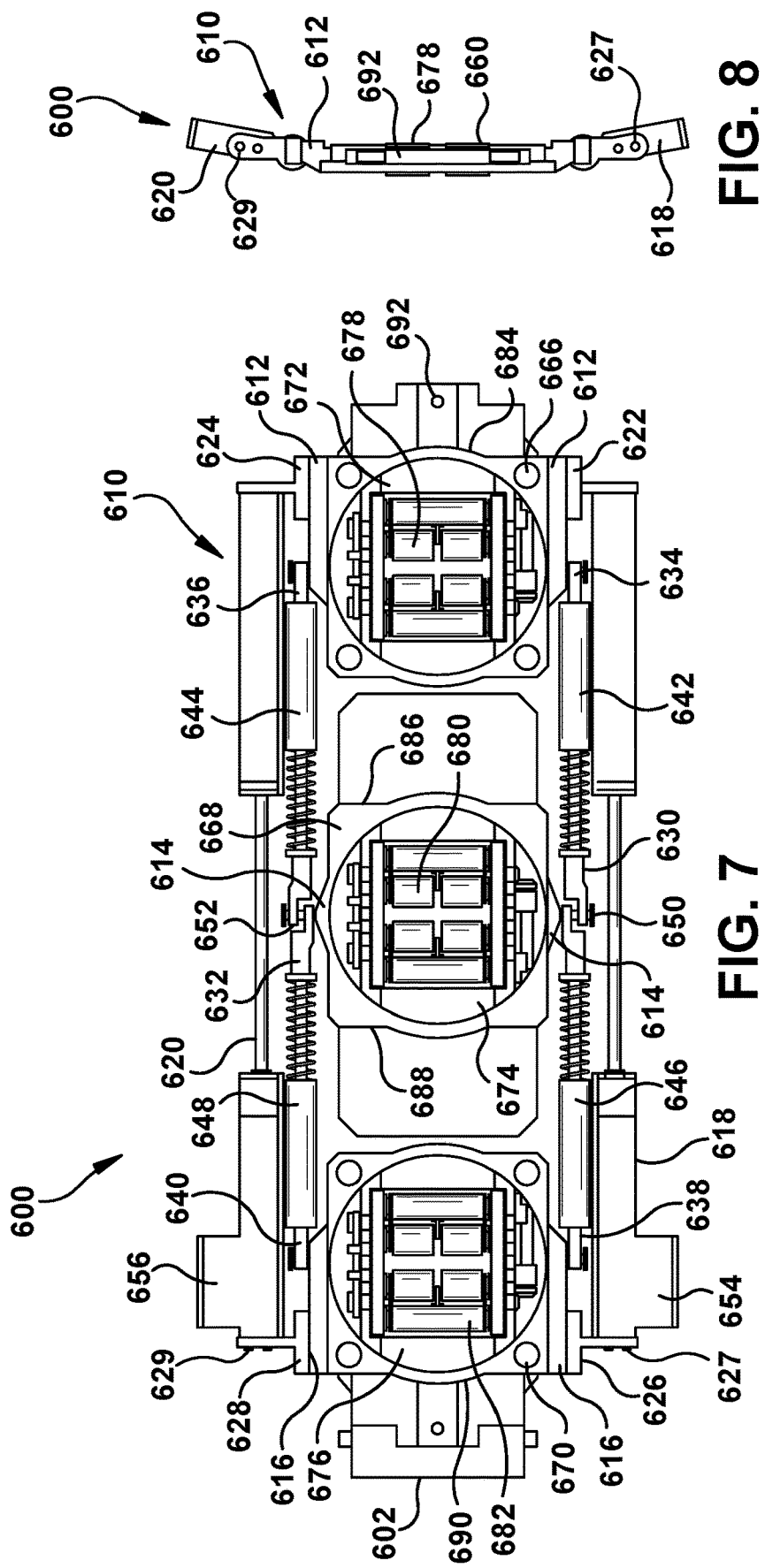

ACTUATED SENSOR MODULE AND METHOD FOR IN SITU GAP INSPECTION ROBOTS

BACKGROUND OF THE INVENTION

The disclosure relates to inspection of machinery and, more specifically, inspection using a robot inserted into an annular gap space, such as an air gap, in a generator, electric motor, or turbomachine, including turbo-generators.

The disclosure is related to concurrently filed U.S. patent application Ser. No. 15/652,730, entitled "MODULAR CRAWLER ROBOT FOR IN SITU GAP INSPECTION" filed Jul. 18, 2017, the entire contents of which are incorporated herein by reference. The disclosure is related to concurrently filed U.S. patent application Ser. No. 15/652,771, entitled "END REGION INSPECTION MODULE AND METHOD FOR IN SITU GAP INSPECTION ROBOT SYSTEM" filed Jul. 18, 2017, the entire contents of which are incorporated herein by reference. The disclosure is related to concurrently filed U.S. patent application Ser. No. 15/652,859, entitled "OMNIDIRECTIONAL TRACTION MODULE FOR A ROBOT" filed Jul. 18, 2017, the entire contents of which are incorporated herein by reference. The disclosure is related to concurrently filed U.S. patent application Ser. No. 15/652,680, entitled "IN SITU GAP INSPECTION ROBOT SYSTEM AND METHOD" filed Jul. 18, 2017, the entire contents of which are incorporated herein by reference.

A visual, mechanical, and/or electrical inspection and testing of a generator, electric motor, or turbomachine should be performed on a periodic basis. For example, generators may be inspected and tested periodically in the field for stator wedge tightness, visual surface anomalies, electromagnetic core imperfections, etc. Generator/stator inspection and testing procedures may require complete disassembly of the stator and removal of the generator rotor from the stator before any inspections or tests can be performed on the unit. The cost of disassembly and removal of the rotor, the time it takes for this process, and the dangers of rotor removal may impact the frequency of such inspections.

In situ inspection of generators has been performed employing poles, trolleys, scopes, and rotor turning techniques. These procedures may not accomplish the inspection task in a complete, timely, or safe manner.

Use of a robotic crawler capable of insertion through the radial air gap between the core iron and the retaining ring permits in situ inspection of the rotor and the stator core. The crawler may be inserted in a collapsed position into the gap and expanded by spring return pneumatic rams to the width of the air gap. The crawler may be remotely controlled by a technician and provides video cameras and other inspection tools to perform generator rotor and stator inspections within the air gap as the crawler is driven to selected locations. The crawler may be maneuvered by the technician within the air gap using video for both navigation and visual inspection.

The stator of a typical generator includes a plurality of stator bars. The stator bars are placed in slots, and are held in place in the slots by various components. For example, a resilient member, such as a ripple spring, is placed between a stator bar and a stator wedge in the slot. The stator wedge is retained in the slot at a required preload tightness by the resilient member, to ensure that the stator bar remains securely in place. During in situ maintenance of generators, the amount of preload that the stator wedges are being subjected to requires monitoring. During operation of the generator, the stator wedge can creep and/or the resilient member can wear and lesson the amount of preload, which can cause stator bars to loosen. In one testing method, a known force is applied to the stator wedge, the displacement of the stator wedge is measured, and the relationship between the force and displacement may be used to determine the health of the stator wedge and/or need for repair or replacement.

BRIEF DESCRIPTION OF THE INVENTION

A first aspect of this disclosure provides a system for in situ gap inspection with an actuated sensor module. A robot is configured to navigate within a gap of a machine, the gap being defined by opposed surfaces within the machine. A sensor module connected to the robotic crawler that includes a mounting interface attached to the robot controller and at least one arm operatively connected to the mounting interface. The arm has a first joint. A sensor head is operatively connected to the at least one arm at the first joint and a first actuator is operatively connected to the at least one arm for moving the sensor head around the first joint.

A second aspect of the disclosure provides a method for in situ gap inspection with an actuated sensor module. A robot is inserted into a gap of a machine having a surface-of-interest. The robot moves to a position adjacent the surface-of-interest to position a sensor module connected to the robot. The robot pivots a sensor head of the sensor module around a first pivot with a first actuator to a desired sensor head position perpendicular to the surface-of-interest. An inspection test is performed on the surface-of-interest using the sensor head.

A third aspect of the disclosure provides an actuated sensor module for an in situ gap inspection robot system. The sensor module includes a mounting interface attached to the robot system and a least one arm operatively connected to the mounting interface and having a first joint. A sensor head is operatively connected to the at least one arm at the first joint and a first actuator is operatively connected to the at least one arm for moving the sensor head around the first joint.

The illustrative aspects of the present disclosure are arranged to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which:

FIG. 7 shows a top view of the robotic crawler of FIG. 6 in its collapsed state.

FIG. 8 shows an end view of the robotic crawler of FIG. 6 in its collapsed state.

Figure 1:
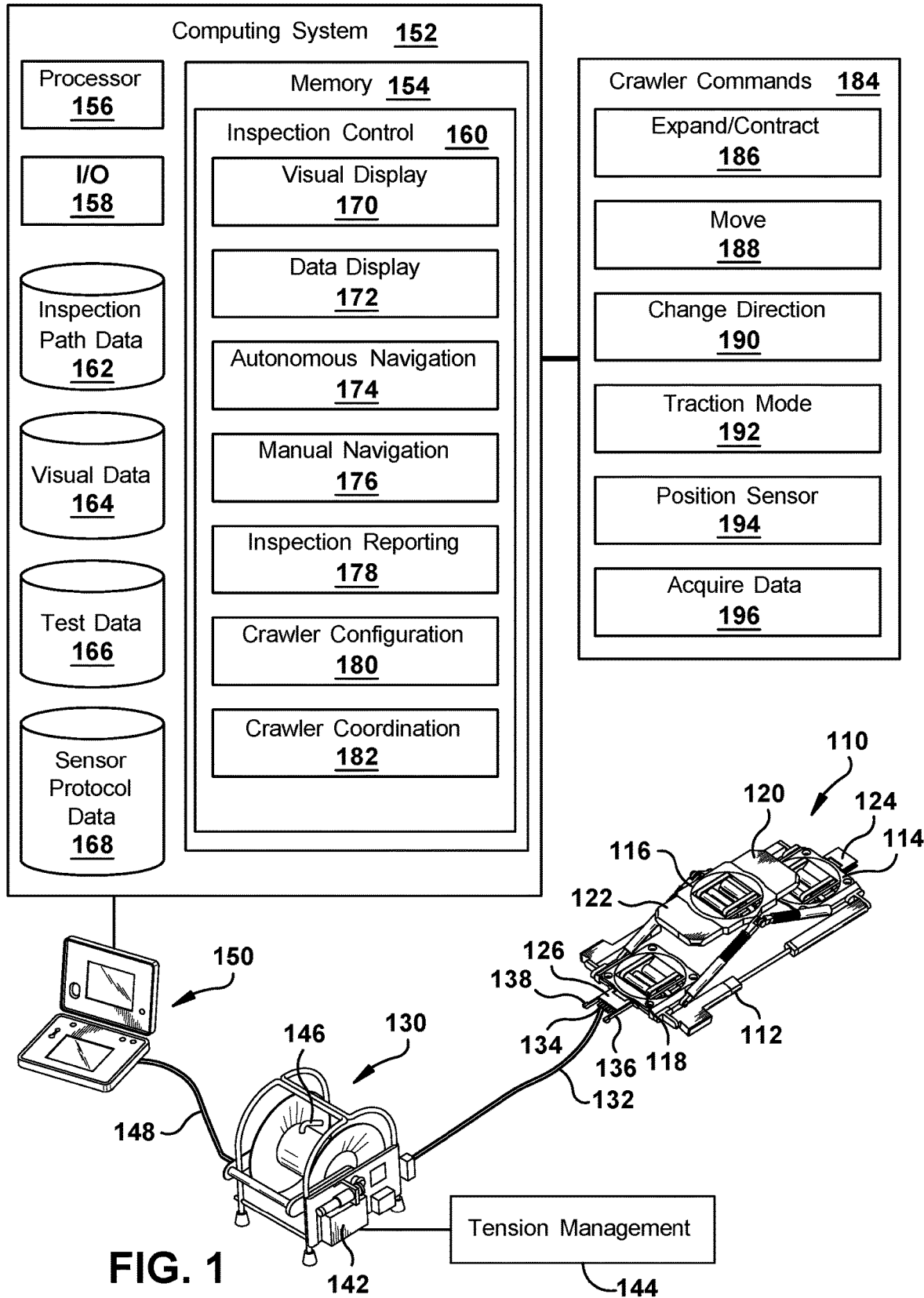
FIG. 1 shows a diagram of an example system for in situ gap inspection according to various embodiments of the disclosure.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings and it is to be understood that other embodiments may be used and that changes may be made without departing from the scope of the present teachings. The following description is, therefore, merely illustrative.

Where an element or layer is referred to as being "on," "engaged to," "disengaged from," "connected to" or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Referring to FIG. 1, an example system 100 for in situ gap inspection is shown. System 100 may include a robotic crawler 110, a tether reel 130, and a control unit 150. Robotic crawler 110 may be configured to be inserted through an entrance gap into an annular gap in a machine to conduct autonomous or semi-autonomous inspection of the machine. For example, robotic crawler 110 may be a collapsible robot that can operate in a collapsed or expanded state and may be inserted through a narrow entrance gap in its collapsed state and expand to a wider gap width such that it engages the opposed surfaces of the annular gap. Robotic crawler 110 is shown in its expanded state in FIG. 1. Once in the annular gap, robotic crawler 110 may navigate the annular gap and use one or more sensor modules to conduct various inspection tests during its movements or at various desired crawler positions in the annular gap. Robotic crawler 110 may be configured for multidirectional movement, including forward and reverse movement in the axial direction and bi-directional lateral movement in the radial direction. In some embodiments, robotic crawler 110 may be configured for omnidirectional movement that includes bi-directional movement in any orientation between the axial and radial directions, in addition to the axial and radial directions. For example, robotic crawler 110 may be configured to move in any direction in a 360 degree arc and freely change its direction of travel to any orientation in the 360 degree arc, including a plurality of directions between and angled from the axial and radial directions. In some embodiments, robotic crawler 110 may include a tether 132 connected to robotic crawler 110 and extending out of the machine during operation. For example, tether 132 may be a cable connected to robotic crawler 110 and enable retrieval of robotic crawler 110 in the event that robotic crawler 110 cannot navigate out of the annular gap under its own power. In some embodiments, tether 132 may provide a physical connection from robotic crawler 110 for a wired communication channel and/or a remote power source and/or pneumatic or hydraulic lines to support test systems or robotic operation. Tether reel 130 may be automated to adjust the tension and/or slack on tether 132 during operation of robotic crawler 110 within the annular gap, enabling robotic crawler 110 to navigate various navigation paths and perform inspection routines without a user manually managing the position of the tether. Control unit 150 may be in communication with robotic crawler 110 to provide control signals to robotic crawler 110 and receive sensor, navigation, and/or other operational data from robotic crawler 110. In some embodiments, control unit 150 may be electrically connected to tether 132 directly or through tether reel 130 and the electrical connection may include one or both of a power channel and a communication channel. Control unit 150 may provide a user interface for a user to monitor, evaluate, supplement, and/or control robotic crawler 110 during an inspection deployment within the annular gap of the machine.

In some embodiments, robotic crawler 110 is a modular robot that may be reconfigured for different inspection tasks and enabling efficient maintenance, replacement, and/or upgrade of individual modules. Robotic crawler 110 may include a body frame, such as an expandable body 112, for receiving, positioning, and connecting various modules relative to one another. In some embodiments, expandable body 112 accommodates a plurality of traction modules 114, 116, 118. For example, robotic crawler 110 may include three traction modules 114, 116, 118, a forward traction module 114, a middle traction module 116, and a rear traction module 118, where forward traction module 114 and rear traction module 118 are configured to engage a first surface in the annular gap and the middle traction module 116 is configured to engage an opposed second surface in the annular gap. Traction modules 114, 116, 118 may be multidirectional traction module capable of moving robotic crawler 110 in multiple directions, including both axial and radial movement within the annular gap. Robotic crawler 110 may further include a plurality of sensor modules 120, 122, such as visual sensors for navigation and/or visual inspection. For example, sensor modules 120, 122 may be attached via sensor interfaces on the forward and rear sides of middle traction module 116 and may provide both forward and rear facing navigation cameras, as well as one or more upward facing cameras for inspecting the adjacent surface of the annular gap. Robotic crawler 110 may also include one or more tether connectors 124, 126 for detachably receiving tether 132, generally with a compatible end connector 134 and fasteners 136, 138.

In some embodiments, tether reel 130 is an automated tether reel that may receive, release, and spool tether 132 to adjust tension as needed during operation of robotic crawler 110. For example, tether reel 130 may include a servo motor 142 and tension management logic 144. For example, servo motor 142 operating in a torque/current control mode may detect changes in tension on tether 132 as it enters tether reel 130 and tension management logic 144 may provide an algorithm for maintaining an acceptable tension range using servo motor 142 to reel in or reel out tether 132 under closed loop control. In some embodiments, tether 132 may have a fixed connection 146 to tether reel 130 and a separate wire 148 may connect to control unit 150. For example, wire 148 may provide communication and/or power channels without providing the mechanical characteristics desired for tethering robotic crawler 110. In some embodiments, tether reel 130 may provide an interface for receiving control signals for tether reel 130 from control unit 150. For example, control unit 150 may be able to adjust tension control or motor parameters and/or manually override operation of tether reel 130. In some embodiments, robotic crawler 110 may operate without a tether, carry its own power (e.g. batteries), and/or use wireless communication with control unit 150.

In some embodiments, control unit 150 may include a computing system 152. Computing system 152 may provide a plurality of programmatic controls and user interface for operating robotic crawler 110. In some embodiments, computing system 152 is a general purpose computing devices, such as a personal computer, work station, mobile device, or an embedded system in an industrial control system (using general purpose computing components and operating systems). In some embodiments, computing system 152 may be a specialized data processing system for the task of controlling operation of system 100. Computing system 152 may include at least one memory 154, processor 156, and input/output (I/O) interface 158 interconnected by a bus. Further, computing system 152 may include communication with external I/O device/resources and/or storage systems, including connected system, such as robotic crawler 110, tether reel 130, and network resources. In general, processor 156 executes computer program code, such as inspection control module 160, that is stored in memory 154 and/or a storage system. While executing computer program code, processor 156 can read and/or write data to/from memory 154, storage systems, and I/O devices (through I/O interface 158). The bus provides a communication link between each of the components within computing system 152. I/O devices may comprise any device that enables a user to interact with computing system 152 (e.g., keyboard, pointing device, display, etc.). Computing system 152 is only representative of various possible combinations of hardware and software. For example, the processor may comprise a single processing unit, or be distributed across one or more processing units in one or more locations, e.g., on a client and server. Similarly, memory and/or storage systems may reside at one or more physical locations. Memory and/or storage systems can comprise any combination of various types of non-transitory computer readable storage medium including magnetic media, optical media, random access memory (RAM), read only memory (ROM), etc. In some embodiments, computing system 152 is a laptop computer in communication with robotic crawler 110 via a wired (serial, USB, Ethernet, etc.) or wireless (802.11, Bluetooth, etc.) connection and running application software for system 100. In some embodiments, some or all of the functions of computing system 152 may be on board robotic crawler 110 using an integrated computing system, such as an on board control module, with or without wireless communication to one or more user interfaces and/or remote data storage.

In some embodiments, computing system 152 may include one or more application programs, data sources, and/or functional modules for controlling robotic crawler 110. For example, computing system 152 may include inspection control module 160 that operates in conjunction with data sources 162, 164, 166, 168 to provide control signals to and receive data from robotic crawler 110. Inspection control module 160 may provide a visual display module 170. For example, visual data collected by cameras on robotic crawler 110 may be displayed by visual display module 170, such as a graphical user interface for one or more video feeds. In some embodiments, visual data from robotic crawler 110 may be stored in visual data source 264 for use by visual display module 170 and/or selective, temporary, and/or archival storage of visual data for later use, including use by other users or systems. Data display module 172 may provide display, including visual display, of other test data, including processed visual data and resulting calculations or analysis. For example, data display module 172 may include a graphical user interface for test results from one or more test protocols using sensor and navigation data from robotic crawler 110. In some embodiments, test data from robotic crawler 110 may be stored in test data source 166 for use by data display module 172 and/or selective, temporary, and/or archival storage of test data for later use, including use by other users or systems. Data display module 172 may include a real-time display of test data as it is collected by robotic crawler 110 and/or one or more functions for viewing, aggregating, analyzing, visualizing, selecting, and/or reporting test data from test data source 166. Autonomous navigation module 174 may provide a protocol or series of commands for navigation of robotic crawler 110 within the annular gap of the machine. In some embodiments, autonomous navigation module 174 enables a user to select an inspection path from a plurality of inspection paths stored in inspection path data source 162. For example, inspection paths may be defined as physical paths robotic crawler 110 should follow within the annular gap to complete one or more inspection tasks in one or more locations within the annular gap. Inspection paths may be based on a physical schematic or parameters of one or more machines defining axial and radial distances. Inspection paths may also include parameters and locations related to specific features of interest for either navigation (e.g., surface features to be avoided) or for testing (e.g., locations or corresponding crawler positions for conducting specific tests). In some embodiments, inspection paths may be stored and defined in terms of a sequence of crawler commands. Autonomous navigation module 174 may enable autonomous navigation by robotic crawler 110 receiving and executing a sequence of crawler commands without user intervention once the autonomous operation initiated. In some embodiments, autonomous navigation module 174 may have completely autonomous inspection routines that require no user intervention once initiated or may include a plurality of inspection subroutines, such as specific movement patterns, position changes, or test protocols, that are initiated in a desired sequence by a user, potentially based on navigational, visual, or test data feedback. Manual navigation module 176 may provide a user with the ability to pilot or otherwise control robotic crawler 110. In some embodiments, manual navigation module 176 may be provided for establishing an initial position for initiating automated control and/or allow a user to override automated control in response to problems, exceptions, or specific test protocols (such as an initial test result that requires further data gathering). In some embodiments, control unit 150 may include one or more user I/O interfaces for manually controlling robotic crawler 110, such as joysticks and other tactile controls, for navigation, deploying sensors, and conducting various test protocols. Inspection module 178 may provide a plurality of routines for various inspection protocols using one or more sensor modules. In some embodiments, one or more sensor protocols are stored in sensor protocol data source 168 for use by inspection module 178. For example, a visual inspection protocol may include activating and capturing visual data from one or more sensor modules on robotic crawler 110 along a defined navigation path to enable mapping of captured visual data to location information with the machine. In some embodiments, a plurality of cameras with varying facings and/or positionable cameras may be present in one or more sensor modules and a visual inspection module may include selective activation and positioning of robotic crawler 110 and its various cameras. An inspection protocol executed by inspection module 178 may include a combination of navigational elements (navigation path, autonomous positioning, and/or manual positioning) and sensor protocols (position requirements, deployment, activation, timing/sampling, parameters, etc.). In some embodiments, inspection module 178 may define the storage of visual data and test data in visual data source 164 and test data source 166 and/or the display of visual data by visual display module 170 and test data by data display module 172. Crawler configuration module 180 may provide data regarding the configuration of modules and related capabilities and protocols for any given configuration of robotic crawler 110. In some embodiments, crawler configuration module 180 may map crawler configurations to machine specifications and sensor protocols to assist a user in matching inspection protocols with the resources available for a given test deployment. For example, a given configuration of sensor modules may define the test capabilities of robotic crawler 110 and recommend specific inspection protocols to utilize those sensor modules. In some embodiments, crawler configuration module 180 may include a library of sensor modules and related capabilities and support user reconfiguration of robotic crawler 110 for a desired inspection protocol. Crawler configuration module 180 may also define the set of crawler commands 184 that may be used to control robotic crawler 110. Crawler coordination module 182 may enable inspection control module 160 to control more than one robotic crawler 110 simultaneously. In some embodiments, crawler coordination module 182 may maintain a plurality of communication channels for control signals and data signals with a plurality of robotic crawlers. For example, crawler coordination 180 may manage a plurality of instances of visual display module 170, data display module 172, autonomous navigation module 174, manual navigation module 176, inspection module 178, and crawler configuration module 180 for parallel management of the plurality of robotic crawlers. In some embodiments, crawler coordination module 182 may include interference protection for tracking the current crawler positions, navigation paths, and timing of various movements and sensor protocols to prevent collisions or other interference within the annular gap.

In some embodiments, visual display module 170, data display module 172, autonomous navigation module 174, manual navigation module 176, and inspection module 178 may include issuing one or more crawler commands 184 to robotic crawler 110 to complete some aspect of their function. Crawler commands 184 may then be translated into messages or control signals from control unit 150 to robotic crawler 110. In some embodiments, crawler configuration module 180 may define the set of crawler commands available to the other modules based on the configuration of robotic crawler 110. An example set of crawler commands 184 are provided, but will be understood to be neither exclusive nor exhaustive of the possible crawler commands that could be used to control robotic crawler 110 and various configurations of traction modules, sensor modules, and body frame mechanics possible. Robotic crawler 110 may receive expand/contract commands 186 to expand or contract expandable body 112 between a collapsed state and one or more expanded states, such as a control signal to one or more motors that drive the body position. In some embodiments, expand or contract may be based on feedback from sensors within robotic crawler 110 when the traction modules are in a planar position (for collapsed state) or have contacted opposed surfaces in the annular gap (for expanded state). In other embodiments, expand or contract may be based on time (e.g. activate motor for x seconds of expansion or contraction) or distance (e.g., set crawler width to y inches). Robotic crawler 110 may receive move commands 188 to drive its traction modules forward or backwards (based on the present alignment of the traction modules in the case of multidirectional traction modules). Robotic crawler 110 may receive change direction commands 190 to reorient its traction modules and direction of travel. For example, change direction commands 190 may allow multidirectional traction modules to rotate 90 degrees and change from axial orientation and directions of travel to radial orientation and directions of travel. In some embodiments, change direction commands 190 may include orientation changes of greater or less than 90 degrees and include a feedback signal for confirming orientation or traction modules and communicating orientation back to control unit 150. Robotic crawler 110 may receive traction mode commands 192 to drive changes in the configuration of the traction modules for different traction modes. For example, traction modules may include a flat mode for robot insertion and/or low profile and smooth surface travel and a clearance mode for providing clearance between the body of robotic crawler 110 and the surfaces it is moving along and/or traversing obstacles or uneven surfaces. Traction mode commands 192 may include control signals to change from flat mode to clearance mode or from clearance mode to flat mode. Robotic crawler 110 may receive position sensor commands 194 for sensor modules that include deployment and/or positioning features. For example, some sensor modules may include electromechanical features for extending, raising, lowering, rotating, or otherwise positioning one or more elements of the sensor module before, during, or after data collection. Position sensor commands 194 may include a control signal to activate a motor for extending or otherwise repositioning a sensor from robotic crawler 110 to position it for data collection or for moving a sensor (such as by rotation) independent of changing crawler position during data collection. Robotic crawler 110 may receive acquire data commands 196 for initiating data collection through a sensor module using whatever modality is present in that sensor module. Acquire data commands 196 may provide a start or stop signal for a continuous data collection mode, such as a video feed from the camera(s) of a visual sensor, or a specific test sequence for a more discrete sensor test, such as a mechanical wedge tightness test. It will be understood that some robotic crawlers and control units may be able to communicate and manage multiple commands in parallel, as overlapping sequences, or as serial command series. Crawler coordination module 182 may enable control unit 150 to issue commands to and acquire data from multiple robotic crawlers in parallel.

Figure 2:
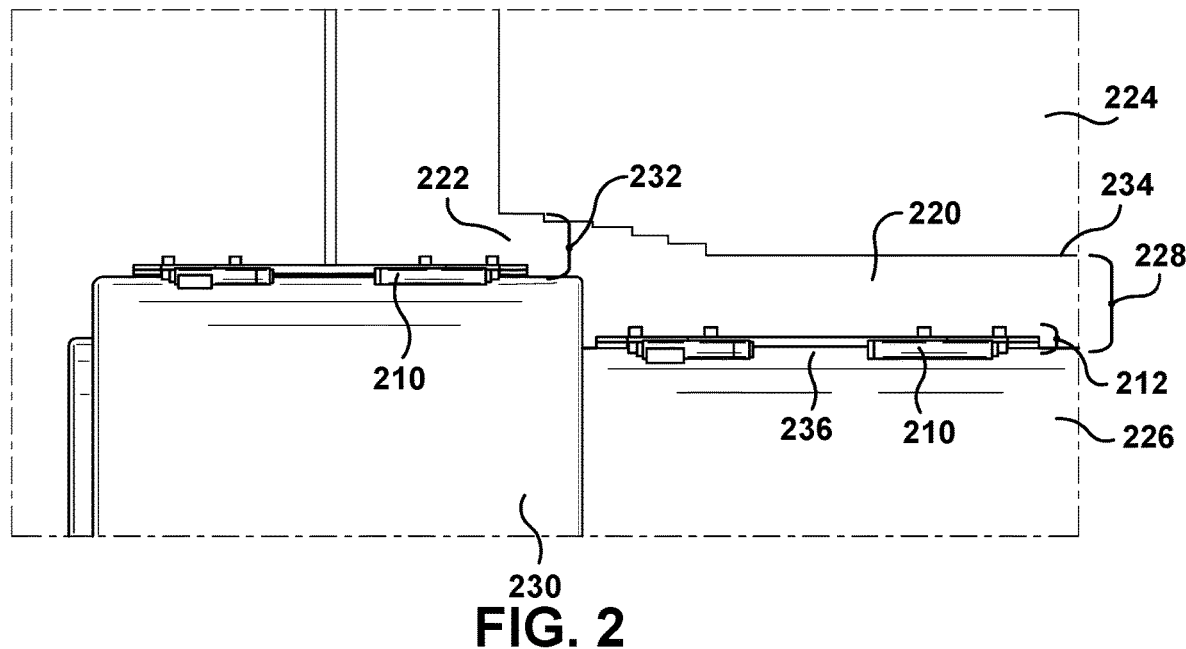
FIG. 2 shows a side section view of gap insertion of a robotic crawler into a machine.

Referring to FIG. 2, an in situ gap inspection system 200 is shown with a robotic crawler 210, such as robotic crawler 110 in FIG. 1, being inserted into a machine 220. Machine 220 may be any machine with an annular gap 220 accessible through an entrance gap 222 and, more specifically, a variety of machine configurations of generators, electric motors, or turbomachines. For example, a generator may allow insertion through the radial air gap between the core iron and the retaining ring permits in situ inspection of the rotor and the stator core. Annular gap 220 may be defined between a cylindrical central member 226 and a surrounding cylindrical member 224 with generally complementary curvature. In some embodiments, annular gap 220 may be an air gap generally defined by: (the inner diameter of the stator minus the outer diameter of the rotor) divided by two. Annular gap 220 has an axial length from a first end to a second end of cylindrical central member 226 and a circumference measured radially around the circumference of cylindrical central member 226. Annular gap 220 has an annular gap width 228 measured from outer surface 236 of cylindrical central member 226 to the nearest opposite surface (inner surface 234) of surrounding cylindrical member 224. In some embodiments, entrance gap 222 may be an air gap at an end of the central cylindrical member 226 and have the same entrance width as annular gap width 228. In other embodiments, entrance gap 222 may include additional features, such as a retaining member 230, that further constrain entrance gap 222 and define an entrance gap width 232 is that is less than annular gap width 228. In some embodiments, additional features or obstacles may reduce annular gap width 228, such entrance baffles used to direct cooling air flow.

In FIG. 2, robotic crawler 210 is in a collapsed state, where its traction modules are aligned in a single plane. Robotic crawler 210 is shown outside entrance gap 222 before insertion and inside annular gap 220 after insertion. Robotic crawler 210 may define a collapsed crawler width 212. Collapsed crawler width 212 may be less than both entrance gap width 232 and annular gap width 228. In its collapsed state, robotic crawler 210 engages only outer surface 236 of central cylindrical member 226 inside annular gap 220.

Figure 3:
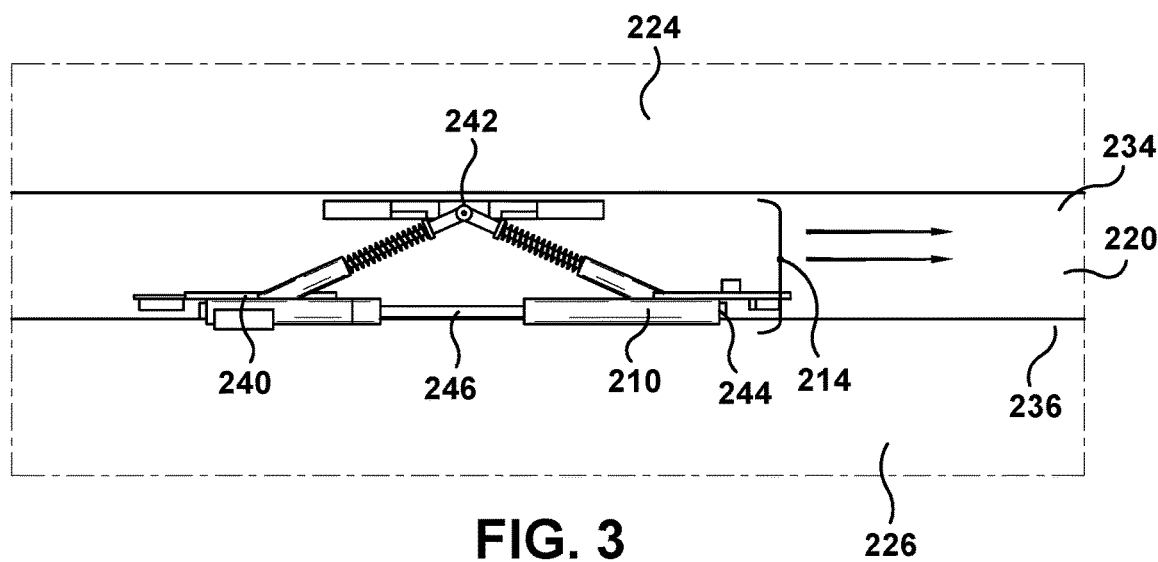
FIG. 3 shows a side section view of an expanded robotic crawler in the annular gap of a machine.
Figure 4:
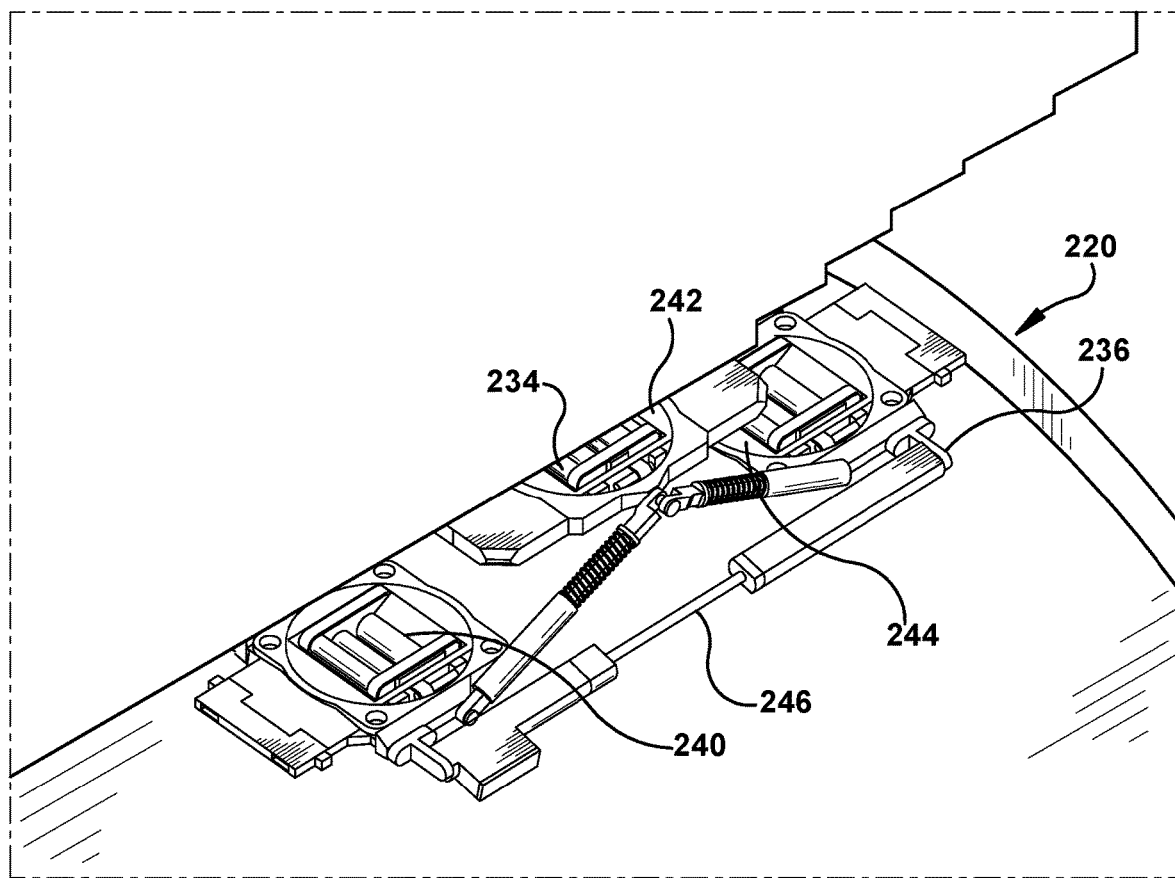
FIG. 4 shows a perspective cutaway view of an expanded robotic crawler in the annular gap of a machine.

FIGS. 3-4 show two views of robotic crawler 210 in an expanded state within annular gap 220. When robotic crawler 210 is in its expanded state, it may engage opposed surfaces 234, 236. In an expanded state, robotic crawler 210 may define an expanded crawler width 214. Expanded crawler width 214 may be larger than collapsed crawler width 212 and entrance gap width 232, and equal to annular gap width 228 such that surface contact may be maintained with opposed surfaces 234, 236. In some embodiments, robotic crawler 210 comprises a plurality of traction modules 240, 242, 244 mounted in an expandable body 246. Traction modules 240, 244 may engage only outer surface 236 of central cylindrical member 226 and traction module 242 may engage only inner surface 234 of surrounding cylindrical member 236. In some embodiments, the configuration of traction modules 240, 242, 244 may be reversed and traction modules 240, 244 may engage only inner surface 234 of surrounding cylindrical member 236 and traction module 242 may engage only outer surface 236 of central cylindrical member 226. Traction modules 240, 242, 244 may include rollers, including wheels, balls, or tracks, to move robotic crawler 210 through annular gap 220 based on moving surface contact with opposed surfaces 234, 236. Traction modules 240, 242, 244 may move robotic crawler 210 on a desired navigation path through annular gap 220.

Figure 5A:
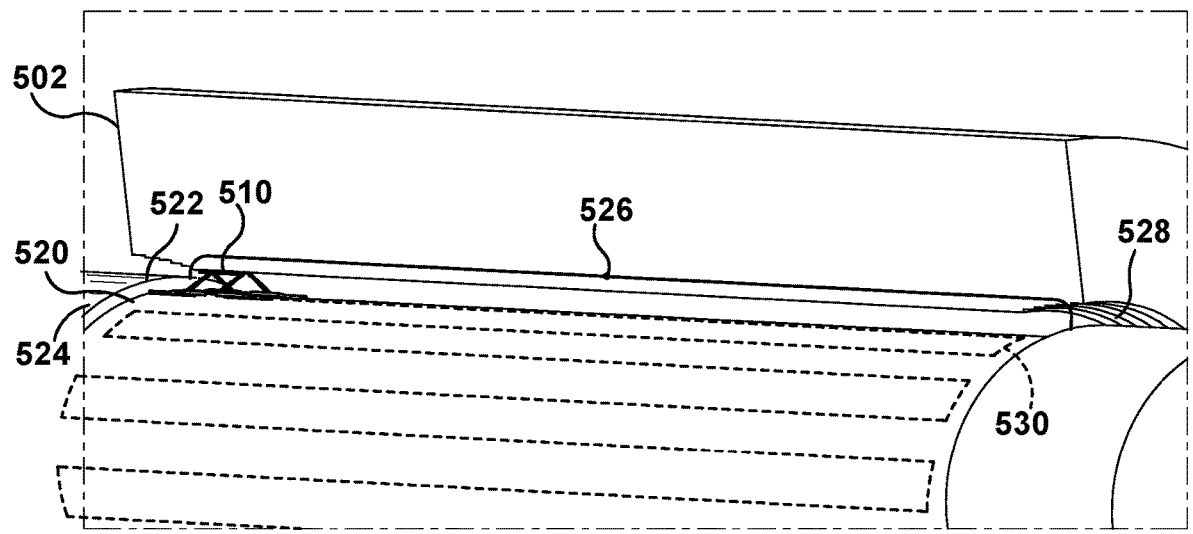
FIGS. 5A and 5B shows example inspection paths of a robotic crawler in the annular gap of a machine according to various embodiments of the disclosure.
Figure 5B:
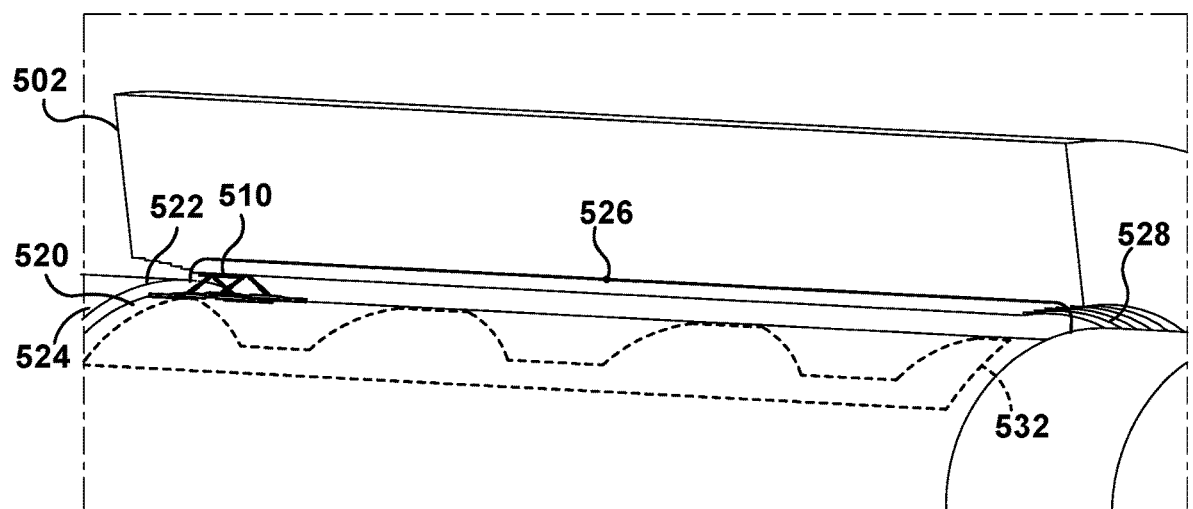

Referring to FIGS. 5A and 5B, another embodiment of a robotic crawler 510 is shown in an annular gap 520 with lines 530, 532 showing example navigation paths for inspecting annular gap 520. Robotic crawler 510 is shown in an expanded state in a starting crawler position just inside entrance gap 522 adjacent an entrance end portion 524 of the machine 502. Following line 530, robotic crawler 510 moves in a forward axial direction along a gap length 526 of annular gap 520 from the entrance end portion 524 to the closed end portion 528. In some embodiments, robotic crawler 510 may reach a step or other obstacle representing the end of the navigable gap length 526 of annular gap 520. For example, closed end portion 528 may include a step created by a retaining ring or other feature and may include another air gap into an enclosed end region of the machine. Robotic crawler 510 may include multidirectional traction modules that enable it to change its travel direction from the axial direction to the radial direction. Line 530 shows a number of radial steps along the circumference of annular gap 520. The length of the radial step may depend on a variety of factors related to sensor range/area (or field of view for visual sensors), test locations, desired test coverage or sampling, and/or specific machine features to be included in the navigation path to support desired test protocols using the sensor modules on robotic crawler 510. After a new radial position is achieved, line 530 shows a return path in the reverse axial direction along gap length 526. Robotic crawler 510 may reorient its movement direction back to an axial orientation and move in the opposite direction down the length of annular gap 520. In some embodiments, robotic crawler 510 may reach a step or other obstacle associated with entrance gap 522 and representing the end of the navigable gap length 526 of annular gap 520. Robotic crawler 510 may again reorient its travel direction for radial movement and make another radial step. Robotic crawler 510 may continue stepping through these axial passes at various radial positions along the circumference for the area of annular gap 520 to be inspected with the selected sensor modules and inspection protocol. In some embodiments, robotic crawler 510 may traverse gap length 236 in radial positions providing overlapping coverage for visual inspection around the entire circumference of annular gap 520 to provide a complete visual inspection of the surfaces of annular gap 520. Following line 532 shows an alternate inspection path and is provided to demonstrate that a plurality of inspection paths may be enabled by multidirectional and omnidirectional movement. Line 532 takes robotic crawler 510 along an inspection path that includes axial travel, radial travel, and travel along intermediate orientations between the axial and radial directions. More complex and less repetitious inspection paths may be used for inspection of specific areas or features, as well as to navigate around known obstacles.

Figure 6:
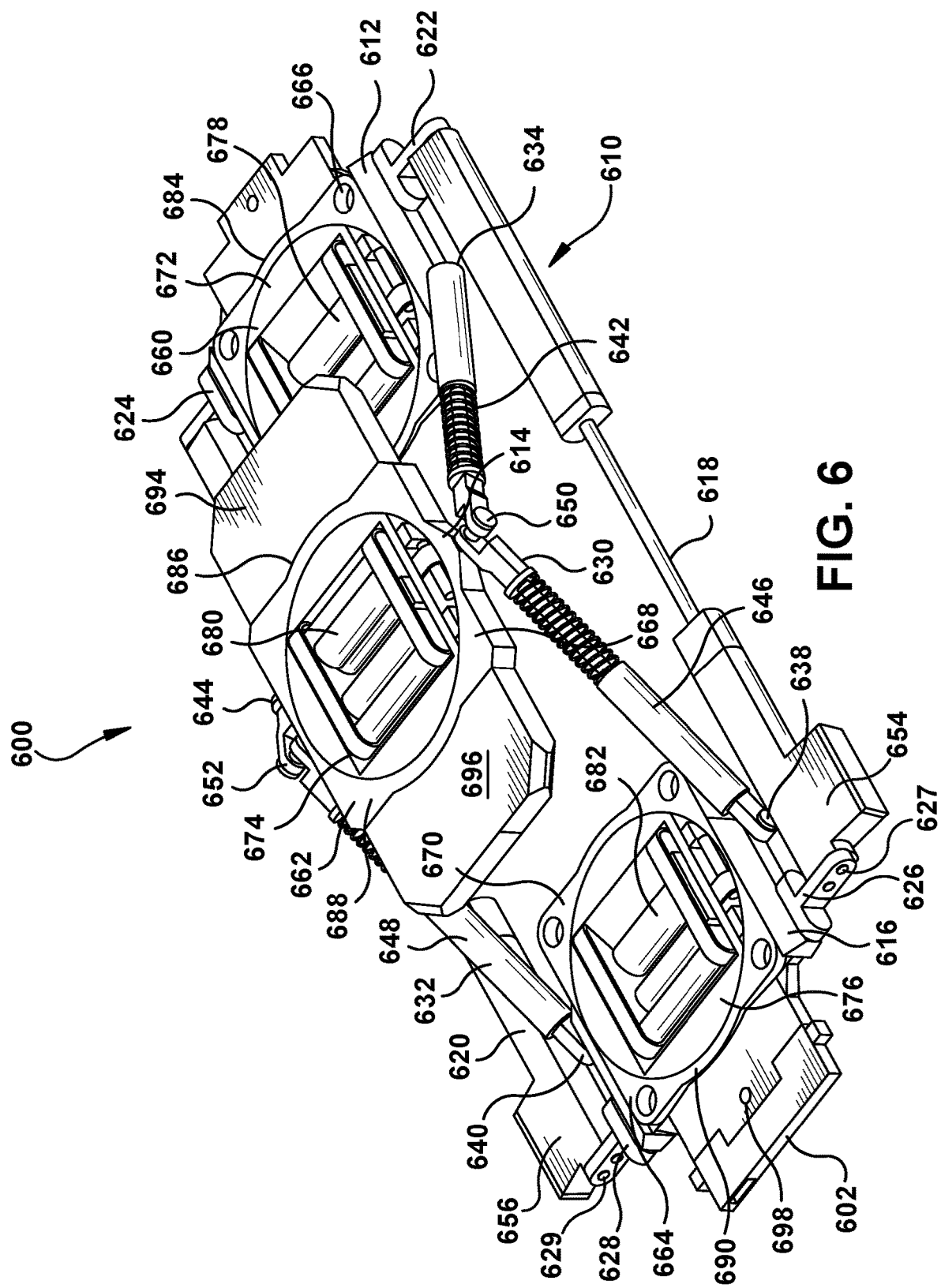
FIG. 6 shows a perspective view of a robotic crawler in its expanded state according to various embodiments of the disclosure.

Referring to FIGS. 6-8, an additional embodiment of a robotic crawler 600 is shown in several views and including an expanded state in FIG. 6 and a collapsed state in FIGS. 7-8. In some embodiments, robotic crawler 600 is a modular robot with an expandable body 610 including plurality of frames 612, 614, 616 for accommodating removable modules. Removable modules may include traction modules 660, 662, 664 that provide rollers, such as wheels, tracks, or balls, or another form of locomotion for moving robotic crawler 600 along the surfaces within a gap. Robotic crawler 600 may also accommodate a plurality of sensor modules, such as navigation sensors, visual inspection sensors, structural test sensors, or electrical test sensors, using sensor interfaces that provide mechanical and/or electrical/communication/control between robotic crawler 600 and the sensor modules. For example, one or more module frames may include sensor interfaces and/or the traction modules or other sensor modules may include sensor interfaces for chaining multiple modules from a single frame. The plurality of sensor interfaces may be provided at several positions on robotic crawler 600 to provide different operating positions for various sensors. For example, each of traction modules 660, 662, 664 may include one or more sensor interfaces and related sensor positions. In some embodiments, there may be multiple configurations of sensor interfaces. For example, sensor interfaces for attachment to traction modules 660, 662, 664 may be different than sensor interfaces between serial sensor interfaces. Other modules may also be provided for other functions, such as a tether connector module 602.

In some embodiments, expandable body 610 includes generally rectangular base frame and includes lateral members 618, 620 on the long sides of the rectangle, connected to front frame 612 and rear frame 616 providing the short sides of the rectangle. Lateral members 618, 620 may include frame attachments 622, 624, 626, 628 proximate their respective distal ends. Frame attachments 622, 624 may connect to front frame 612 and frame attachments 626, 628 may connect to rear frame 616. In some embodiments, middle frame 614 may be configured to be displaced from the plane of front frame 612 and rear frame 616 to expand the width of expandable body 610 in its expanded state. Middle frame 614 may be attached to extension link members 630, 632, which are connected to the rectangular base frame. For example, extension link members 630, 632 may include pivoting attachments 634, 636, 638, 640 with front frame 612 and rear frame 616 or, alternately, with lateral members 618, 620 proximate their distal ends. Extension link members 630, 632 may be articulated link members with first links 642, 644 and second links 646, 648 having pivoting attachments 650, 652 to middle frame 614. Pivoting attachments 650, 652 may act as an articulated joint in extension link members 630, 632 and move middle frame 614 perpendicular to the plane of the rectangular base frame. Expandable body 610 may include a motor or other actuator for moving middle frame 614. For example, lateral members 618, 620 may include linear actuators 654, 656 for moving front frame 612 relative to rear frame 616, changing the lengths of lateral members 618, 620 and the distance between front frame 612 and rear frame 616. When lateral members 618, 620 are in their fully extended positions, front frame 612, middle frame 614, and rear frame 616 may be in the same plane and expandable body 610 is in its narrowest or collapsed state. As lateral members 618, 620 are shortened by linear actuators 654, 656 and rear frame 616 moves toward front frame 612, extension link members 630, 632 articulate at pivoting attachments 650, 652 and first links 642, 644, second links 646, 648, and lateral members 618, 620 form an isosceles triangle with middle frame 614 moving in a direction perpendicular to the direction of movement between front frame 612 and rear frame 616.

Other configurations of expandable bodies are possible, such as one or more frames being mounted on lever arms, scissor jacks, telescoping members, or other displacement mechanisms. In some embodiments, expandable body 610 may incorporate shock absorbers between front frame 612 and rear frame 616 and middle frame 614 to assist in navigating uneven gap spaces. For example, extension link members 630, 632 may incorporate telescoping links with an internal spring to assist with traction on opposed gap surfaces and compensate for some obstacles and/or changes in gap spacing. In some embodiments, lateral members 618, 620 may include emergency releases 627, 629 to disengage lateral members 618, 620 manually in the event of power loss or other failure that prevents control of linear actuators 654, 656. For example, frame attachments 626, 628 may incorporate mechanical fasteners that attach lateral members 618, 620 to frame attachments 626, 628 and these mechanical fasteners may act as emergency releases 627, 629 by enabling a user to release the mechanical fasteners and thereby disengage lateral members 618, 620 to cause expandable body 610 to collapse into its collapsed state. In some embodiments, emergency releases 627, 629 may be screws, bolts, or pins through frame attachments 626, 628 and into lateral members 618, 620 that may be removed to collapse expandable body 610. In some embodiments, expandable body 610 has a lateral shape that is an arc based on the configuration of frames 612, 614, 616 and lateral members 618, 620, most visible in FIG. 8. The arc of expandable body 610 may be configured to complement the curvature of an annular gap in which robotic crawler 600 is intended to operate. For example, the arc or curvature may be similar to the arc of the outer surface of the central cylindrical member or the inner surface of the surrounding cylindrical member that define the annular gap.

In some embodiments, each of frames 612, 614, 616 are configured to receive, position, and retain traction modules 660, 662, 664. For example, traction modules 660, 662, 664 may each be multidirectional traction modules with fixed outer frames 666, 668, 670 to removably attach to frames 612, 614, 616. Traction modules 660, 662, 664 may include rotating inner frames 672, 674, 676 that enable robotic crawler 600 to change the orientation of rollers 678, 680, 682 and direction of movement. Each of traction modules 660, 662, 664 may also include one or more interfaces 684, 686, 688, 690 that may be used to attach sensor modules or other functional modules, directly or in series. For example, traction module 660 may include interface 684 and is shown with a visual sensor module 692. Traction module 662 may include interfaces 686, 688 and visual sensor modules 694, 696. Traction module 664 may include interface 670, visual sensor module 698, and tether connector module 602.

Figure 9:
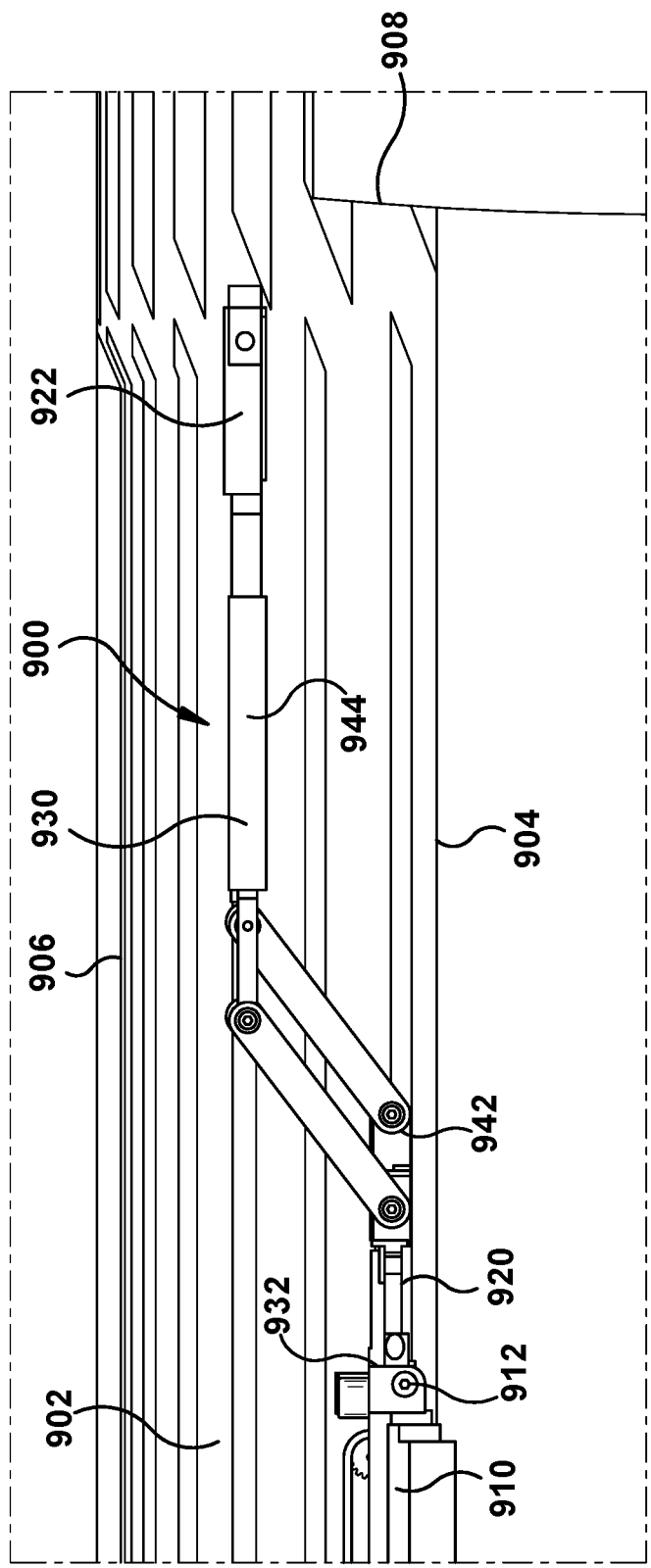
FIG. 9 shows a side section view of an example deployment of a sensor module positioning system in the annular gap of a machine according to various embodiments of the disclosure.

Referring to FIG. 9, a mechanical positioning module 900 is shown. Mechanical positioning module 900 may be used to position a sensor module (not shown) within the gap 902 and relative to a crawler position of a robotic crawler 910. For example, mechanical positioning module 900 may include one or more positionable joints to move a sensor interface 920 (and an attached sensor module) to a desired height between the opposing machine surfaces 904, 906 that define the gap 902. Mechanical positioning module 900 is shown in a gap 902 between a first surface 904 and a second surface 906 and attached to a robotic crawler 910 positioning a sensor interface housing 922 to clear a lip 908. In some embodiments, mechanical positioning module 900 may include a mounting interface housing 930 that connects to a sensor interface 912 of robotic crawler 910. A mechanical positioning assembly 940 may connect to mounting interface housing 930 at one end and sensor interface housing 922 at the other end. For example, mounting interface housing 930 may include a mounting interface 932 similar to those described elsewhere for sensor modules and compatible with one or more sensor interfaces, such as sensor interface 912, on robotic crawler 910. Mounting interface housing 930 may include a motor (not shown) and other components for receiving control signals and controlling the position of mechanical positioning assembly 940. Mechanical positioning assembly 940 may include a variety of positionable joints, members, and actuators for performing the desired positioning operations, such as a parallel lift 942 capable of raising and lowering sensor interface housing 922 while maintaining it on a plane parallel to the base of robotic crawler 910 and extension member 944 for positioning sensor interface housing 922 a desired distance from robotic crawler 910. Sensor interface housing 922 may provide sensor interface 920 similar to those described elsewhere for receiving, positioning, and connecting a sensor module. In some embodiments, sensor interface housing 922 may be replaced with a sensor housing for an integrated sensor module with a positioning assembly.

Figure 10:
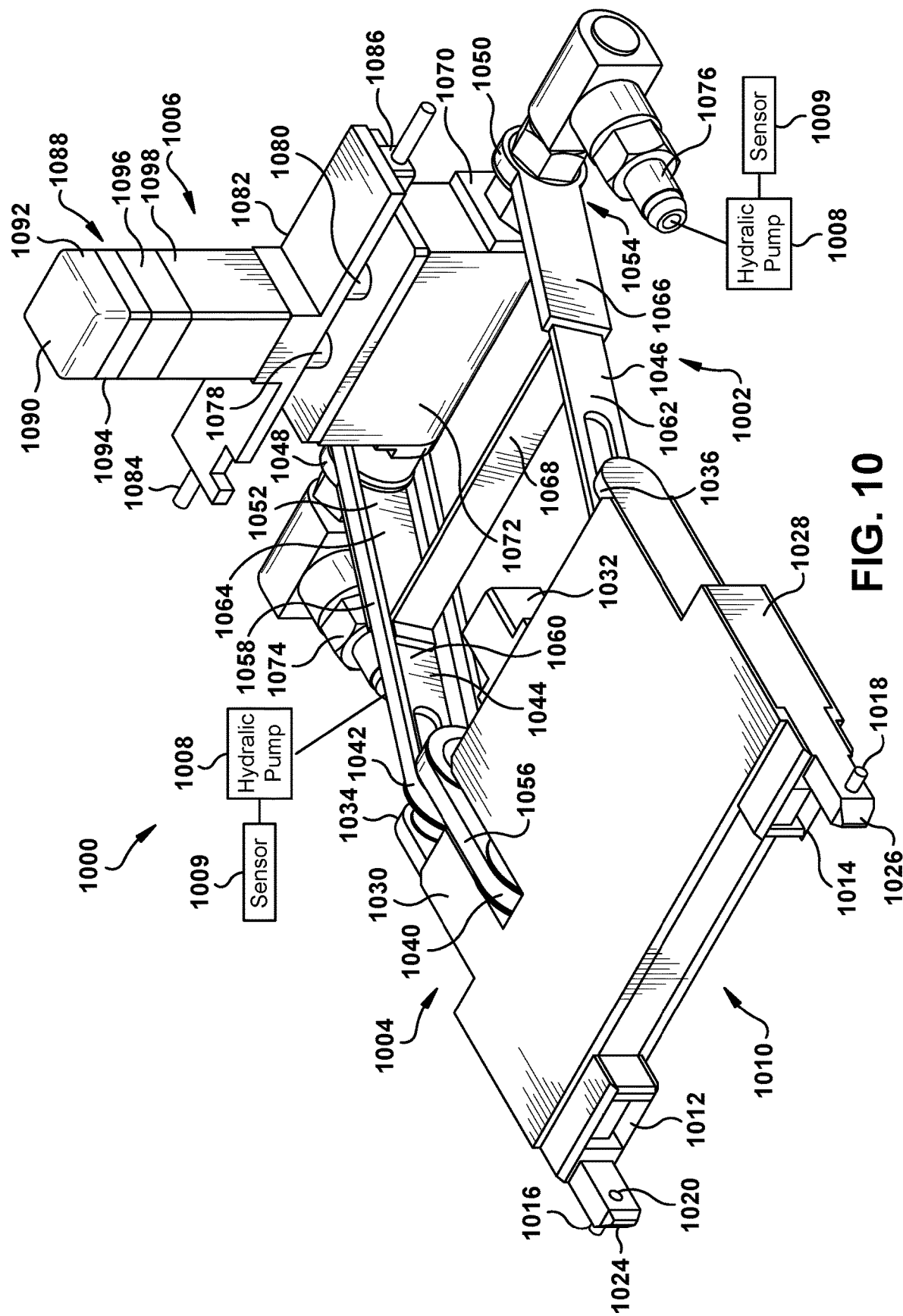
FIG. 10 shows a first perspective view of an example wedge inspection test sensor module according to various embodiments of the disclosure.
Figure 11:
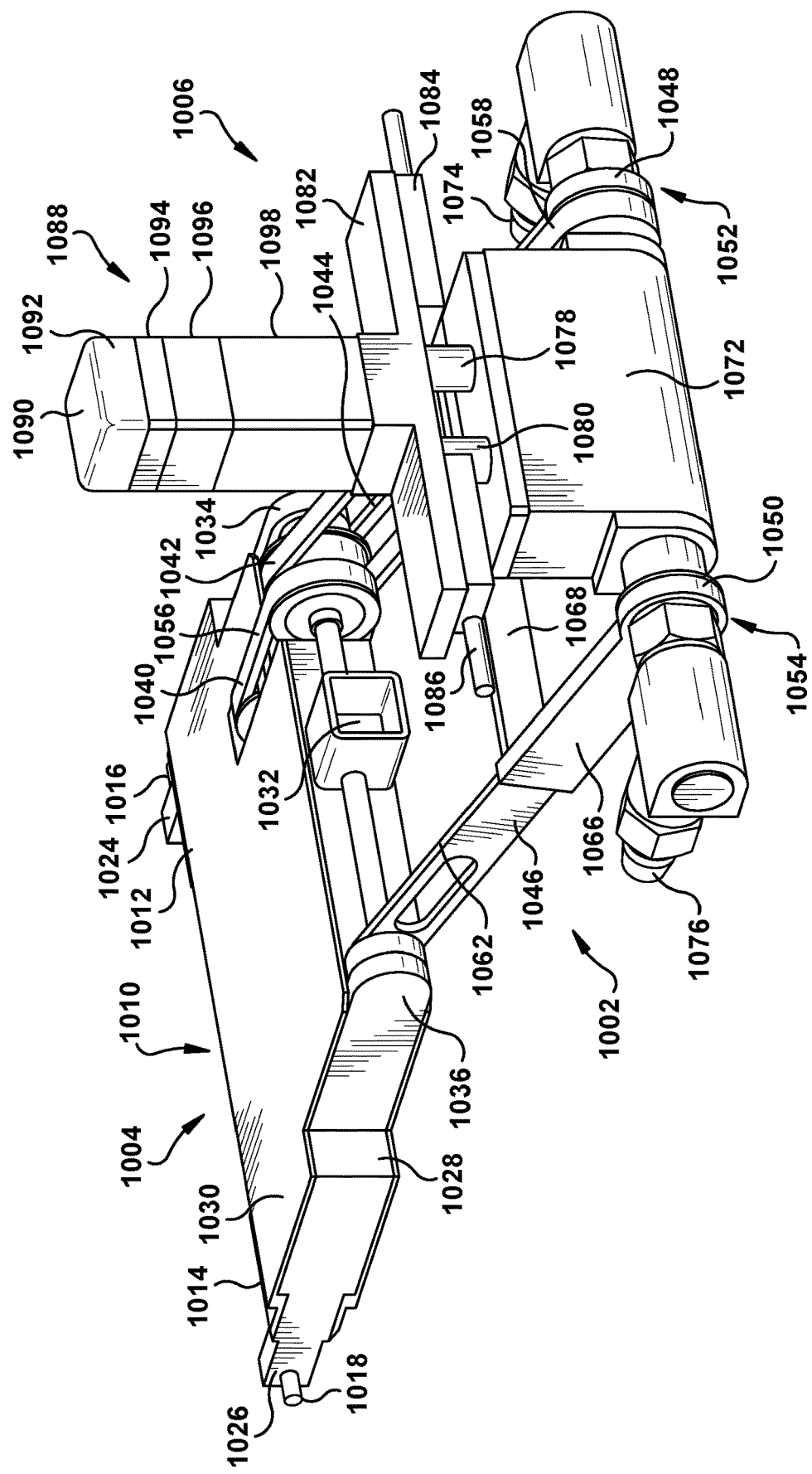
FIG. 11 shows a second perspective view of the example wedge inspection test sensor module of FIG. 10.

Referring to FIGS. 10 and 11, a mechanical test module is shown, more specifically, a wedge inspection test sensor module 1000 for testing wedge tightness using a correlation between applied force and deflection of the stator surface-of-interest, such as a stator wedge. A similar mechanical test module may be used for testing deflection of other surfaces-of-interest in response to an applied force to a moveable component or object inside the stator. Sensor module 1000 may include a mechanical test assembly 1002 attached to a module housing 1004 for attachment to a robot, such as the robotic crawlers described with regard to FIGS. 1-8 herein. In some embodiments, mechanical test assembly 1002 may include a sensor head 1006. The robotic crawlers may be deployed into the gap of a machine and navigate to a desired crawler position based on control signals from the robotic crawler or control unit, placing sensor module 1000 in a test position to conduct the desired mechanical test. For example, sensor module 1000 may be positioned in the gap directly below a stator surface-of-interest, such as a selected stator wedge at a known circumferential and axial position. Mechanical test assembly 1002 may provide test or sensor data back to the robotic crawler or control unit. For example, test or sensor data may be passed through an electrical interconnect between sensor module 1000 and the robotic crawler, data may be sent wirelessly between the two, or data may be provided via wired or wireless transmission directly to the control unit. In some embodiments, a portion of the data for the test may come from sensor module 1000 and another portion of the data may come from another source, such as a force sensor 1009 in an attached hydraulic pump 1008, data from another sensor module on the robotic crawler, or data from another test system or operational sensors within the machine. In some embodiments, module housing 1004 may include onboard electronics (not shown) for processing, storing, and/or transmitting the collected data and/or calculated results, with or without the assistance of another microprocessor located elsewhere.

Module housing 1004 may include a mounting interface 1010. For example, mounting interface 1010 may include electrical interconnects 1012, 1014, such as spring-loaded contact connectors, and fasteners 1016, 1018 for removably attaching sensor module 1000 to a sensor interface on the robotic crawler. In some embodiments, fasteners 1016, 1018 may be inserted through through-holes 1020 (other through-hole not visible) in support brackets 1024, 1026 to attach into corresponding mechanical receptacles in the sensor interface, such as slots accommodating support brackets 1024, 1026 and a threaded hole for receiving threaded ends (not shown) of fasteners 1016, 1018. Electrical interconnects 1012, 1014 may include one or more physical paths, such as wires, carrying various electrical channels. For example, power, control, data, and other communication channels may be included and may include distinct paths for various electrical, sensor, motor, and/or microprocessor systems or subsystems. Module housing 1004 may include a housing body 1028 and a housing cover 1030, supporting and protecting various internal components, including electronics, motors, interconnects, and other components. In some embodiments, module housing 1004 may incorporate a camera 1032 for collecting visual data related to the positioning and operation of sensor module 1000. For example, camera 1032 may be a wide view camera positioned facing sensor head 1006 and providing a field of view that includes sensor head 1006 and the opposed surfaces of the gap in which sensor module 1000 is deployed. Camera 1032 may assist in positioning sensor head 1006 at a desired spacing from the opposed surfaces within the gap of the machine by providing visual data to a user of the control unit or to a visual positioning subsystem in sensor module 1000 or the robotic crawler or control unit. Module housing 1004 includes arm pivots 1034, 1036 for attaching and supporting mechanical test assembly 1002. Module housing 1004 may also include and support at least a portion of actuators 1040, 1042 that move mechanical test assembly 1002, such as motors and gears that drive actuators 1040, 1042.

Mechanical test assembly 1002 may include actuators 1040, 1042, extension arms 1044, 1046, and sensor head 1006. Actuators 1040, 1042 may include a variety of drives for moving and positioning extension arms 1044, 1046 and sensor head 1006. For example, a variety of motors, rotary positioning systems, and similar actuators may move extension arms 1044, 1046 around arm pivots 1034, 1036 on module housing 1004 and/or sensor head 1006 around head pivots 1048, 1050 at distal ends 1052, 1054 of extension arms 1044, 1046. In some embodiments, actuators 1040, 1042 may include timing belts 1056, 1058 connected to motors within module housing 1004. Timing belt 1056 may be operatively connected to extension arms 1044, 1046 at arm pivots 1034, 1036 to move and position extension arms 1044, 1046 around arm pivots 1034, 1036 and control the elevation of sensor head 1006 relative to the opposed surfaces in the gap. Timing belt 1058 may be operatively connected to sensor head 1006 at head pivots 1048, 1050 to move and position sensor head 1006 around head pivots 1048, 1050 on distal ends 1052, 1054 of extension arms 1044, 1046 to control the tilt of sensor head 1006 and allow sensor head 1006 to be positioned perpendicular to the stator surface-of-interest. Timing belts 1056, 1058 may provide compliance in rotating components and minimize joint stress caused by collisions of sensor head 1006 with the environment during navigation and positioning. In some embodiments, extension arms 1044, 1046 may include length adjustments that may allow customization of the positioning arc to the operating width of the air gap. For example, extension arms 1044, 1046 may include fixed members 1060, 1062 and sliding members 1064, 1066 that provide telescoping adjustment of the lengths of the extension arms from arm pivots 1034, 1036 to head pivots 1048, 1050. In some embodiments, the length of extension arms 1044, 1046 may be adjusted manually while sensor module 1000 is outside the gap of the machine or otherwise accessible to a user. In some embodiments, extension arms 1044, 1046 may include a length actuator (not shown) for remotely adjusting the length of extension arms 1044, 1046. Sensor head 1006 may be mounted to and extend between extension arms 1044, 1046 in a direction perpendicular to the lengths of extension arms 1044, 1046 at head pivots 1048, 1050. In some embodiments, extension arms 1044, 1046 may include additional cross-member 1068 attached to extension arms 1044, 1046 and spanning between them perpendicular to the lengths of extension arms 1044, 1046 for additional support, strength, and stability.

Sensor head 1006 may include a base 1070 attached by head pivots 1048, 1050 to extension arms 1044, 1046. For example, base 1070 may include an actuator base 1072 and base interconnects 1074, 1076 arranged along an axis extending through head pivots 1048, 1050. In some embodiments, actuator base 1072 may be a hydraulic actuator base and base interconnects 1074, 1076 may be hydraulic hose fittings. In other embodiments, other controlled force actuators, such as pneumatic or electromechanical actuators, may be used. Interconnects 1074, 1076 may connect to a controlled power source, such as hydraulic pump 1008 for a hydraulic actuator. In other embodiments, an integrated electromechanical actuator driven by electrical power received through electrical interconnects 1012, 1014 may obviate the use of an external power source, such as hydraulic pump 1008, and interconnects 1074, 1076. Other hydraulic, pneumatic, mechanical, or electrical power sources may also be used, depending on the actuator configuration. In some embodiments, hydraulic pump 1008 may include a force sensor 1009 that may be used to generate force data for testing wedge tightness. For example, force sensor 1009 may be an integrated feature of the control loop for hydraulic pump 1008 or may be a separate force sensor on the line or lines connected to interconnects 1074, 1076. In some embodiments, force sensor 1009 may be integrated directly into sensor head 1006, such as within actuator base 1072. Linear actuator members 1078, 1080 may controllably extend from actuator base 1072 to adjust the height of sensor head 1006 in response to the applied force, moving actuator platform 1082 away from actuator base 1072. Actuator platform 1082 may position and support position sensors 1084, 1086 and anvil 1088. For example, position sensors 1084, 1086 may include inductive sensors that generate position data correlating to the displacement of anvil 1088 and, more specifically, contact surface 1090 on anvil head 1092. During a test, contact surface 1090 may engage a surface-of-interest on the stator to measure displacement of the surface-of-interest in response to a known force. In some embodiments, position sensors 1084, 1086 may use proximity to a reference surface or structure to calculate positions and displacement. Other types of positions sensors, including optical (including laser), acoustic, accelerometer, and other proximity sensors may be used. In some embodiments, anvil 1088 may include an adjustable height (independent of actuator members 1078, 1080) to customize the starting height of sensor head 1006 for different gap sizes. For example, anvil 1088 may include a removable anvil head 1092 and a plurality of anvil spacers 1094, 1096, 1098 stacked below anvil head 1092 that may be added or removed to configure a desired starting height. In some embodiments, anvil spacers 1094, 1096, 1098 are part of a set of standard sized anvil spacers, such as a set of six spacers plus the head, that collectively represent the most common variations in stator wedge depths and air gap variations. Combinations of actuator platform 1082, anvil head 1992, and anvil spacers 1094, 1096, 1098 provide an incremental range of heights for anvil 1088 and sensor head 1006.

Figure 12:
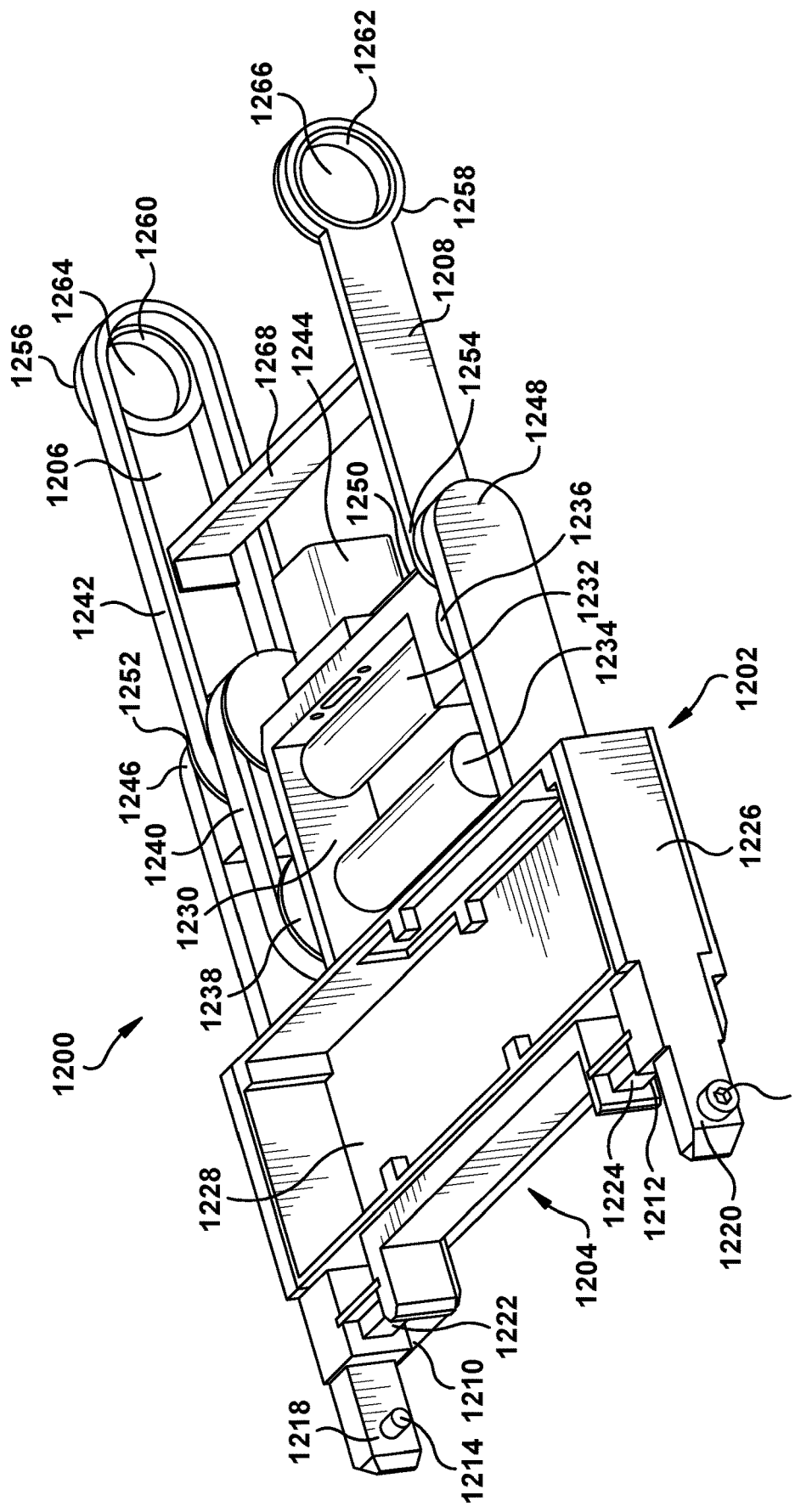
FIG. 12 shows a perspective view of a portion of an example multi-actuator sensor module with a housing cover removed.

Referring to FIG. 12, an example multi-actuator sensor module 1200 is shown with its housing cover, internal wiring and electronics, and sensor head removed. Sensor module 1200 may be described similarly to sensor module 1000 in FIGS. 10-11. Sensor module 1200 includes a module housing 1202 with a mounting interface 1204 and extension arms 1206, 1208. Mounting interface 1204 may include may include electrical interconnects 1210, 1212, such as spring-loaded contact connectors, and fasteners 1214, 1216 for removably attaching sensor module 1200 to a sensor interface on a robotic crawler. In some embodiments, fasteners 1214, 1216 may be inserted through support brackets 1218, 1220 to attach into corresponding mechanical receptacles in the sensor interface. Electrical interconnects 1210, 1212 may include one or more physical paths, such as pins 1222, 1224 connected to wires (not shown), carrying various electrical channels. For example, power, control, data, and other communication channels may be included and may include distinct paths for various electrical, sensor, motor, and/or microprocessor systems or subsystems.

Module housing 1202 may include a housing body 1226 defining an electronics compartment 1228 and a motor compartment 1230. Electronics compartment 1228 may include various electronics and interconnects for receiving electrical signals via electrical interconnects 1210, 1212 and/or other channels, such as wireless channels and/or wired connections to motors, sensors, cameras, light sources, and other subcomponents of sensor module 1200. For example, electronics compartment 1228 may include a printed circuit board with various integrated and/or mounted components, including a microcontroller, one or more power, communication, and/or control interfaces, and/or hubs or buses for managing channels among various components. Motor compartment 1228 may include arm lift motor 1232 and sensor head tilt motor 1234 driving shafts connected to gear assemblies 1236, 1238 and timing belts 1240, 1242. In some embodiments, module housing 1202 may incorporate a camera 1244 and one or more light sources (not shown) and their interconnects may pass through motor compartment 1228. Module housing 1202 may include arm pivots 1246, 1248 for attaching and supporting extension arms 1206, 1208. Module housing 1202 may also accommodate and support gear assemblies 1236, 1238 and at least a portion of the belt paths for timing belts 1240, 1242. Extension arms 1206, 1208 may include a Extension arms 1206, 1208 may be movably attached to module housing 1202 at arm pivots 1246, 1248 such that they may rotate around an axis (not shown) of arm pivots 1246, 1248 based on rotation of gear assembly 1236 under the power of arm lift motor 1232. For example, arm pivots may include recesses (not shown) that accommodate an axel 1250 that supports at least a portion of gear assemblies 1236, 1238 and mounting ends 1252, 1254 of extension arms 1206, 1208. Extension arms 1206, 1208 may have distal ends 1256, 1258 at opposite ends from mounting ends 1250, 1252 that include sensor head pivots 1260, 1262. For example, sensor head pivots 1260, 1262 may include circular openings 1264, 1266 that may accommodate and axel member (not shown) of the sensor head. In some embodiments, extension arms 1206, 1208 may include additional cross-member 1268 attached to extension arms 1206, 1208 and spanning between them perpendicular to the lengths of extension arms 1206, 1208 for additional support, strength, and stability.

In another embodiment (not shown), extension arms 1206, 1208 may be fixed in a position relative to the sensor interface of the robotic crawler that allows operation of sensor module 1200 without adjusting the positions of extension arms 1206, 1208 around pivots 1246, 1248 inside the gap. In some embodiments, pivots 1246, 1248, arm lift motor 1232, and related components may be eliminated and replaced by a fixed attachment of extension arms 1206, 1208 or a more limited height or angular adjustment. In some embodiments, sensor head pivots 1260, 1262 may be integrated into the distal end of module housing 1202 and extension arms 1206, 1208 may be integrated into the side walls of module housing 1202.

Figure 13:
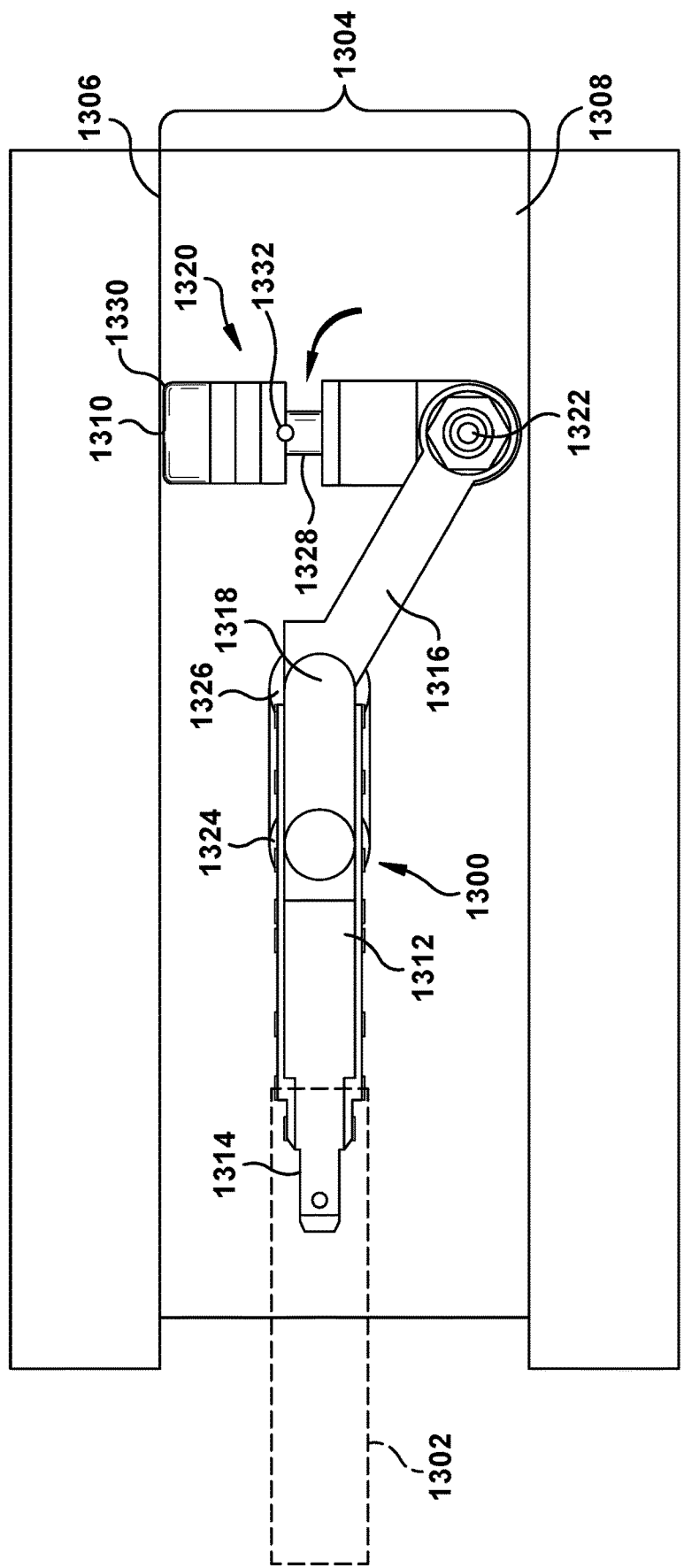
FIG. 13 shows a side view of an example deployment of a multi-actuator sensor module in the annular gap of a machine according to various embodiments of the disclosure.

Referring to FIG. 13, a wedge inspection test sensor module 1300 is shown supported by a robot 1302 and deployed in a gap 1304 between opposing surfaces 1306, 1308. For example, sensor module 1300 may be similar to sensor modules described in FIGS. 10-12 and robot 1302 may be similar to robotic crawlers described in FIGS. 1-8. Gap 1304 may be an annular gap in a machine such as a generator, an electric motor, or a turbomachine and opposing surfaces 1306, 1308 may be the rotor and stator respectively of such machines. For example, surface 1306 may be a stator surface including stator wedges with a surface-of-interest 1310 to be tested. Sensor module 1300 may include a module housing 1312 connected to robot 1302 by a mounting interface 1314. Extension arms 1316 may extend from an arm joint 1318 at the opposite side of module housing 1312 from mounting interface 1314. A sensor head 1320 may extend from a head joint 1322 at the opposite end of extension arms 1316 from module housing 1312. Arm joint 1318 and head joint 1322 may each be controlled by actuators 1324, 1326 that allow them to be rotatably positioned during deployment, navigation, and testing. Sensor head 1320 may include a linear actuator 1328 for applying a measured force to surface-of-interest 1310 through a contact surface 1330 on a distal end of sensor head 1320 and a position sensor 1332 for measuring the displacement of linear actuator 1328 and/or surface-of-interest 1310.

Sensor module 1300 is shown in a test position with contact surface 1330 engaged and in surface contact with surface-of-interest 1310. In some embodiments, robot 1302 may be a robotic crawler inserted through a narrow entrance gap and thickness of robot 1302, including sensor module 1300, may determine feasibility of deploying the robot system in a selected machine. For deployment through the entrance gap, sensor module 1300 may use actuators 1324, 1326 to align module housing 1312, extension arm 1316, and sensor head 1320 in a common plane such that mounting interface 1314 aligns with contact surface 1330, as well as arm joint 1318 and head joint 1322. Once inside gap 1304, robot 1302 may expand or otherwise reposition the sensor interface to which mounting interface 1314 is engaged, such that sensor module 1300 is positioned away from opposing surfaces 1306, 1308. In order to move sensor head 1320 and contact surface 1330 into a test position, actuator 1326 may rotate extension arm 1316 toward surface 1308 and actuator 1324 may begin to rotate sensor head 1320 toward surface 1306. In some deployments, extension arm 1316 may be brought into contact with surface 1308 at head joint 1322. Sensor head 1320 may be rotated toward surface 1306 until sensor head 1320 is perpendicular to surface 1306 and contact surface 1320 is in contact with surface-of-interest 1310. Positioning of extension arm 1316 and sensor head 1320 may be done iteratively until the desired test position is achieved.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A system comprising:
a robot configured to navigate within a gap of a machine, the gap being defined by opposed surfaces within the machine; and
a sensor module connected to the robot, the sensor module including:
a mounting interface attached to the robot;
at least one arm operatively connected to the mounting interface and having a first joint and a second joint, wherein the at least one arm includes a length adjustment mechanism that adjusts a length of the at least one arm between the first joint and the second joint;
a sensor head operatively connected to the at least one arm at the first joint; and
a first actuator operatively connected to the at least one arm for moving the sensor head around the first joint and perpendicularly against one of the opposed surfaces.

2. The system of claim 1, wherein the robot is a robotic crawler having a collapsed state and an expanded state, the gap is an annular gap, and the machine is selected from a generator, an electric motor, or a turbomachine, the collapsed state providing the robotic crawler with a first thickness less than an entrance gap width for the annular gap of the machine and the expanded state providing the robotic crawler with a second thickness greater than the entrance gap width and less than a working gap width for the annular gap of the machine, the first actuator controllably positioning the sensor head in contact with a surface-of-interest of the opposed surfaces within the annular gap.

3. The system of claim 2, wherein one of the opposed surfaces is a stator of the machine with a stator surface, and the first actuator controllably positions the sensor head perpendicular to the stator surface, the sensor head including a wedge tightness inspection system.

4. The system of claim 1, further comprising a second actuator operatively connected to the at least one arm for moving the at least one arm around a second pivot, the second actuator controllably positioning the sensor head at a desired spacing from the opposed surfaces within the annular gap.

5. The system of claim 4, wherein the first actuator is operatively connected to a first motor by a first timing belt and the second actuator is operatively connected to a second motor by a second timing belt.

6. The system of claim 4, wherein the sensor module further comprises an electronics housing, a microcontroller disposed within the electronics housing, a motor housing containing a first motor for the first actuator and a second motor for the second actuator, and at least one electrical interconnect to the robot carrying control signals for the first actuator and the second actuator.

7. The system of claim 1, wherein the sensor module further comprises a camera positioned to view the sensor head and the opposed surfaces within the machine.

8. The system of claim 1, wherein the sensor head includes a contact surface for engaging a surface-of-interest in the gap, a force actuator that controllably applies a force to the surface-of-interest through the contact surface, a displacement sensor that measures the displacement of the surface-of-interest, and at least one data channel transmitting force data from the force actuator and displacement data to the displacement sensor.

9. The system of claim 8, wherein the contact surface is a distal end of an anvil head and the sensor head further comprises a plurality of stackable spacers between the anvil head and the force actuator.

10. The system of claim 8, wherein the force actuator is a hydraulic lift operatively connected to the contact surface and applying the force in a direction perpendicular to the contact surface.

11. The system of claim 8, wherein the displacement sensor is an inductive sensor mounted between the contact surface and the force actuator.

12. A method comprising:
inserting a robot into a gap of a machine having a surface-of-interest;
moving the robot to a position adjacent the surface-of-interest to position a sensor module connected to the robot, the sensor module including at least one arm operatively connected to a mounting surface and having a first joint and a second joint, wherein the at least one arm of the sensor module includes a length adjustment mechanism that adjusts a length of the at least one arm of the sensor module between the first joint and the second joint;
pivoting a sensor head of the sensor module around a first pivot with a first actuator to a desired sensor head position perpendicular to the surface-of-interest; and
performing an inspection test on the surface-of-interest using the sensor head.

13. The method of claim 12, further comprising pivoting the at least one arm of the sensor module around a second pivot with a second actuator to a desired arm position, wherein pivoting the at least one arm includes driving a second motor with a second timing belt operatively connected to the second pivot and pivoting the sensor head includes driving a first motor with a first timing belt operatively connected to the first pivot.

14. The method of claim 12, wherein performing the inspection test includes:
engaging a contact surface of the sensor head to the surface of interest;
controllably applying a force to the surface-of-interest through the contact surface; and
measuring a displacement of the surface-of-interest.

15. The method of claim 14, wherein controllably applying the force includes driving a force actuator to move the contact surface perpendicular to the surface-of-interest and measuring the displacement includes receiving displacement data from a displacement sensor mounted between the contact surface and the force actuator.

16. A sensor module for a robot system comprising: a mounting interface attached to the robot system;
at least one arm operatively connected to the mounting interface and having a first joint and a second joint, wherein the at least one arm includes a length adjustment mechanism that adjusts a length of the at least one arm between the first joint and the second joint;
a sensor head operatively connected to the at least one arm at the first joint; a first actuator operatively connected to the at least one arm for moving the sensor head around the first joint and perpendicular to a surface-of-interest; and
a second actuator operatively connected to the at least one arm for moving the at least one arm around the second joint.

17. The sensor module of claim 16, further comprising an electronics housing, a microcontroller disposed within the electronics housing, a motor housing containing a first motor for the first actuator and a second motor for the second actuator, a camera, and at least one electrical interconnect to the robot carrying control signals for the first actuator and the second actuator and image data from the camera.

18. The sensor module of claim 17, wherein the sensor head includes a contact surface for engaging the surface-of-interest in a gap of a machine, a force actuator that controllably applies a force to the surface-of-interest through the contact surface, a displacement sensor that measures the displacement of the surface-of-interest, and at least one data channel transmitting force data from the force actuator and displacement data the displacement sensor.

19. The sensor module of claim 17, wherein the mounting interface is attached to a robotic crawler configured to navigate within an annular gap of a machine, the machine selected from a generator, an electric motor, or a turbomachine, wherein the robotic crawler has a collapsed state and an expanded state, the collapsed state providing the robotic crawler with a first thickness less than an entrance gap width for the annular gap of the machine and the expanded state providing the robotic crawler with a second thickness greater than the entrance gap width and less than a working gap width for the annular gap of the machine, the second actuator controllably positioning the sensor head at a desired spacing from a stator surface within the annular gap and the first actuator controllably positioning the sensor head perpendicular to the stator surface, the sensor head including a wedge tightness inspection system.

* * * * *